(12) United States Patent
Coati et al.

(10) Patent No.: US 8,162,942 B2
(45) Date of Patent: Apr. 24, 2012

(54) INTRAMEDULLARY NAIL COMPRISING ELEMENTS OF SHAPE-MEMORY MATERIAL

(75) Inventors: Michele Coati, San Pietro in Cariano (IT); Giancarlo Marazzi, Saronno (IT); Graziano Marini, Castel D'Azzano (IT); Graziano Rossi, Verona (IT); Luigi Rossi, Peschiera del Garda (IT); Daniele Verturini, Povegliano Veronese (IT)

(73) Assignee: Orthofix S.r.l. (IT)

( * ) Notice: Subject to any disclaimer, the term of this patent is extended or adjusted under 35 U.S.C. 154(b) by 989 days.

(21) Appl. No.: 10/599,502

(22) PCT Filed: Mar. 31, 2005

(86) PCT No.: PCT/EP2005/003395
§ 371 (c)(1),
(2), (4) Date: Apr. 8, 2008

(87) PCT Pub. No.: WO2005/094706
PCT Pub. Date: Oct. 13, 2005

(65) Prior Publication Data
US 2008/0262495 A1    Oct. 23, 2008

(30) Foreign Application Priority Data

Mar. 31, 2004 (EP) .................... 04007785
Mar. 31, 2004 (EP) .................... 04007786

(51) Int. Cl.
*A61B 17/72* (2006.01)
(52) U.S. Cl. ......................................... 606/63
(58) Field of Classification Search ............... 606/62–68
See application file for complete search history.

(56) References Cited

U.S. PATENT DOCUMENTS

| | | | | |
|---|---|---|---|---|
| 5,415,660 A * | 5/1995 | Campbell et al. | ............... | 606/62 |
| 5,702,215 A | 12/1997 | Li | | |
| 6,077,264 A * | 6/2000 | Chemello | .................. | 606/67 |
| 6,261,289 B1 * | 7/2001 | Levy | .................. | 606/63 |
| 6,488,684 B2 * | 12/2002 | Bramlet et al. | .................. | 606/62 |
| 6,575,973 B1 | 6/2003 | Shekalim | | |
| 7,828,802 B2 * | 11/2010 | Levy et al. | .................. | 606/63 |
| 2004/0230193 A1 * | 11/2004 | Cheung et al. | .................. | 606/63 |
| 2005/0159749 A1 * | 7/2005 | Levy et al. | .................. | 606/72 |
| 2005/0187555 A1 * | 8/2005 | Biedermann et al. | .................. | 606/72 |

FOREIGN PATENT DOCUMENTS

| | | |
|---|---|---|
| DE | 38 38 388 A1 | 5/1990 |
| EP | 0 772 420 | 5/1997 |

(Continued)

*Primary Examiner* — Eduardo C Robert
*Assistant Examiner* — Jerry Cumberledge
(74) *Attorney, Agent, or Firm* — Akerman Senterfitt

(57) ABSTRACT

An intramedullary nail (10, 110, 210, 310, 410, 510, 610) suitable for insertion in a fractured elongate bone (12), of the type comprising a stem (14, 114, 214, 314, 414, 514, 614) extended between a proximal end (16, 116, 216, 416, 516, 616) and a distal end (18, 118, 218, 418, 518, 618). The nail comprises a plurality of elements (20, 120, 220, 320, 420, 520, 620) realized with at least one shape-memory material, a plurality of seats (19, 119, 219, 319, 419, 519, 619) formed in the stem (14, 114, 214, 314, 414, 514, 614) for housing the elements (20, 120, 220, 320, 420, 520, 620). The elements (20, 120, 220, 320, 420, 520, 620) are suitable to take a first shape wherein they are retractably housed in the respective seats (19, 119, 219, 319, 419, 519, 619) and a second shape wherein they project from the respective seats (19, 119, 219, 319, 419, 519, 619).

6 Claims, 20 Drawing Sheets

FOREIGN PATENT DOCUMENTS

| | | | |
|---|---|---|---|
| FR | 2 727 304 A | 5/1996 |
| FR | 2 783 702 A | 3/2000 |
| JP | 10-57398 A | 3/1998 |
| WO | WO 03/007830 A1 | 1/2003 |

* cited by examiner

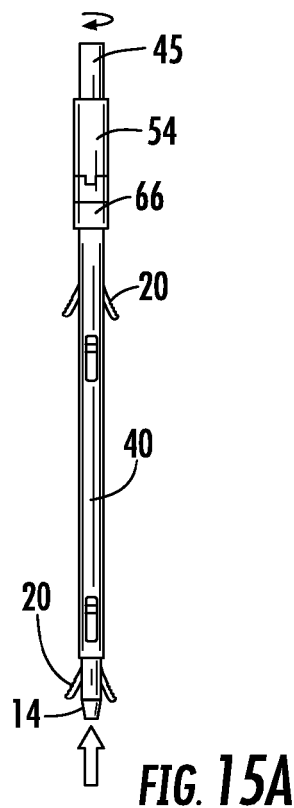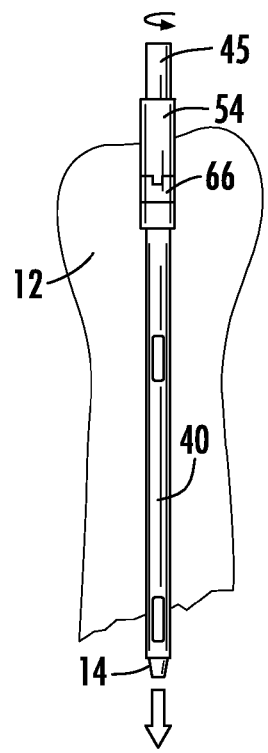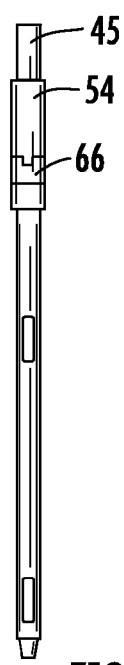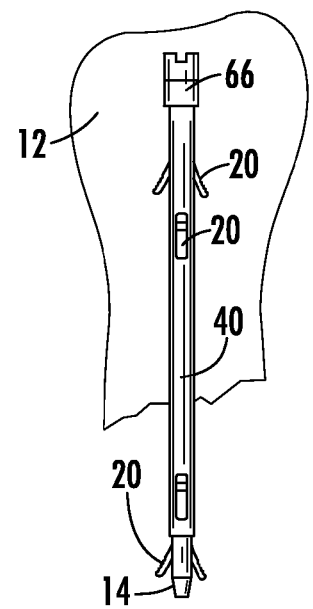
FIG. 15A
FIG. 15C
FIG. 15B
FIG. 15D

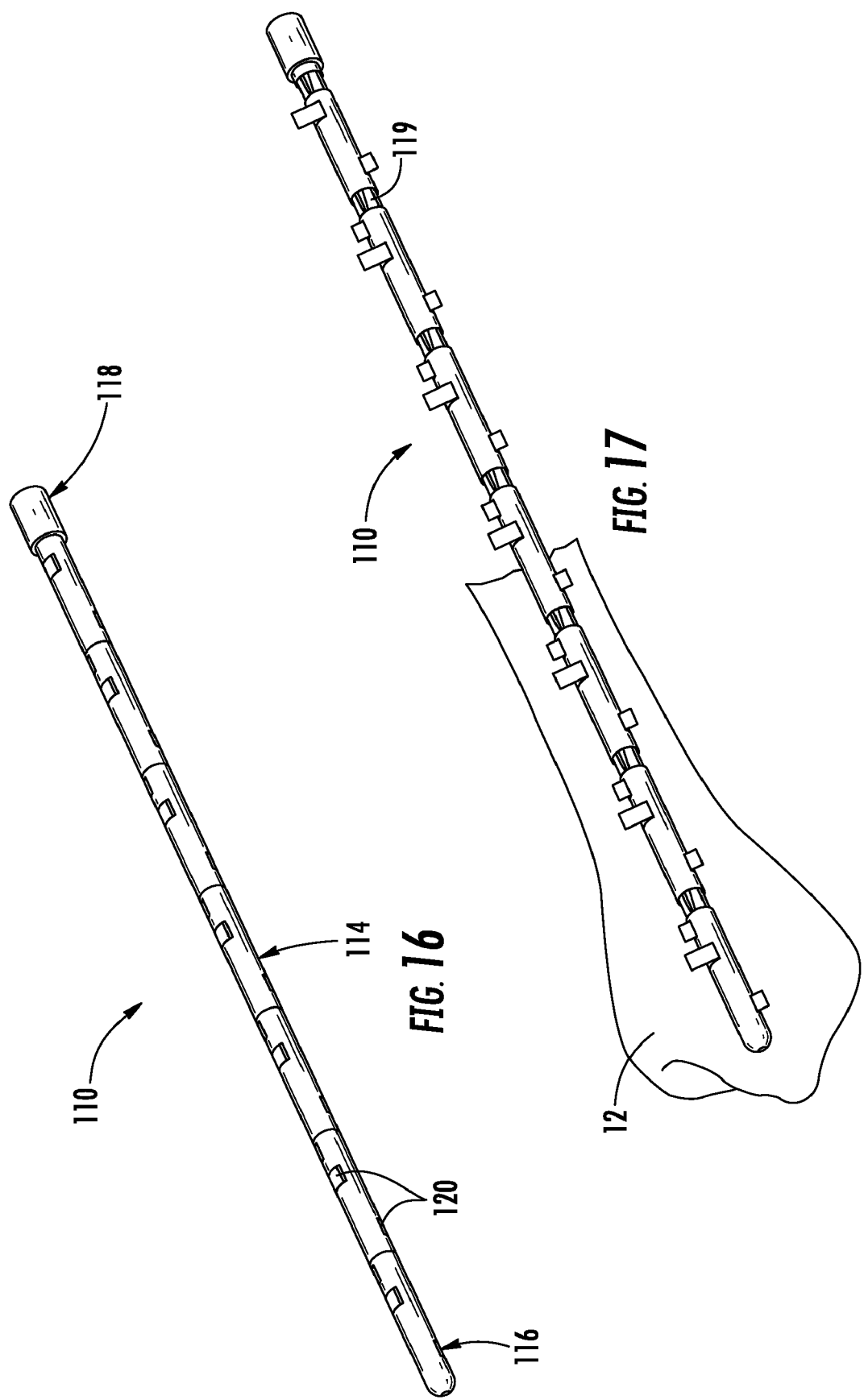

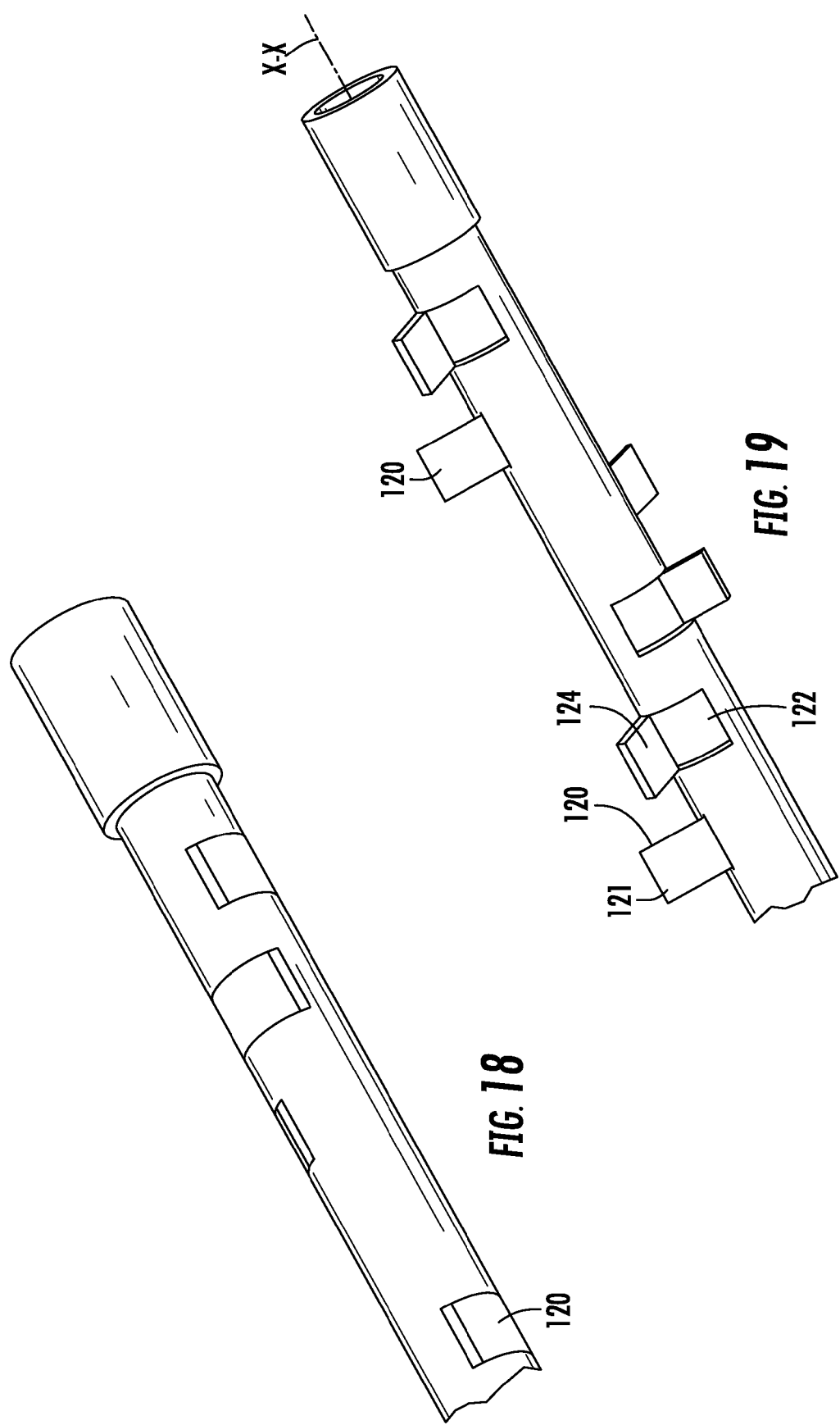

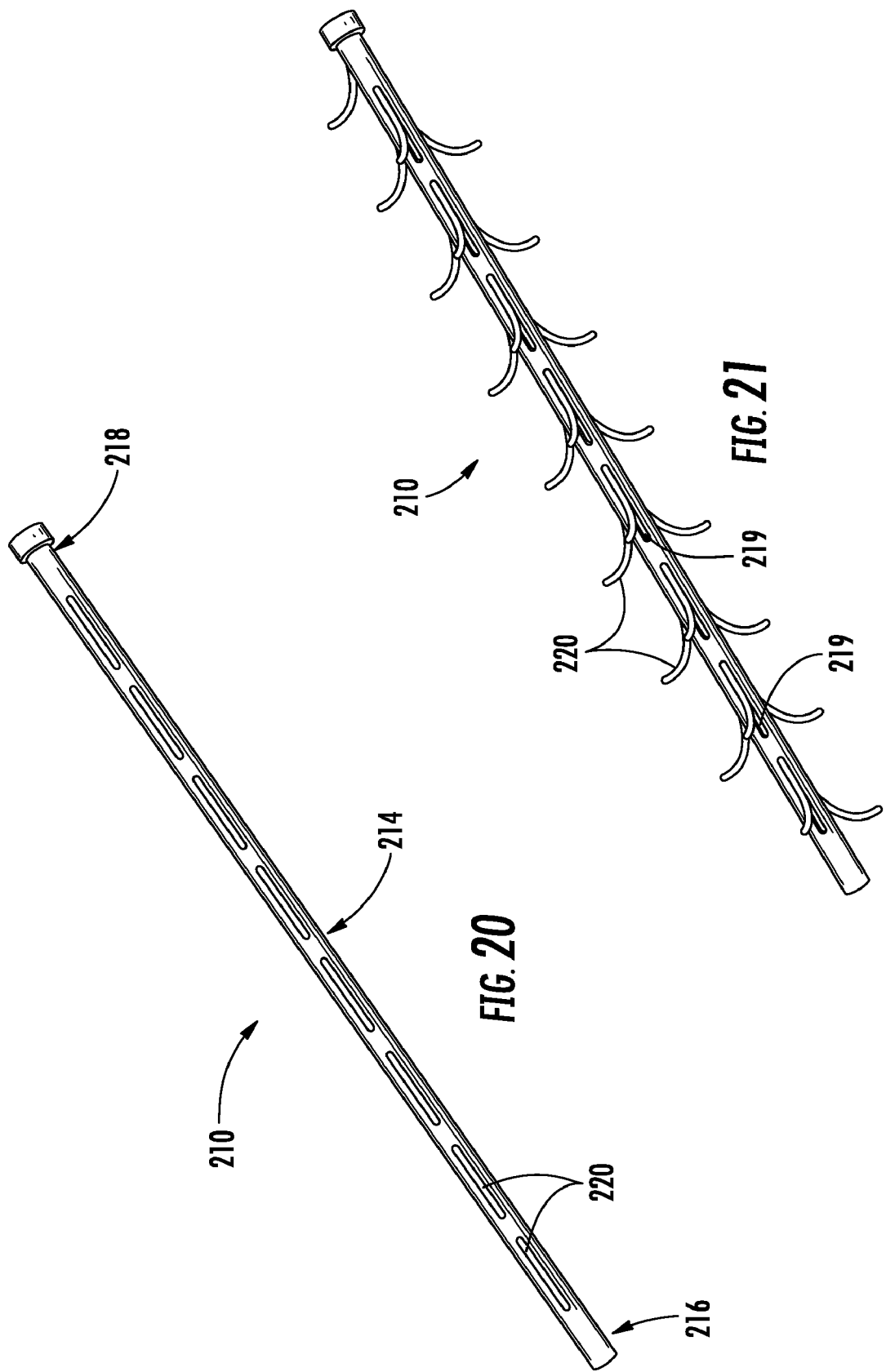

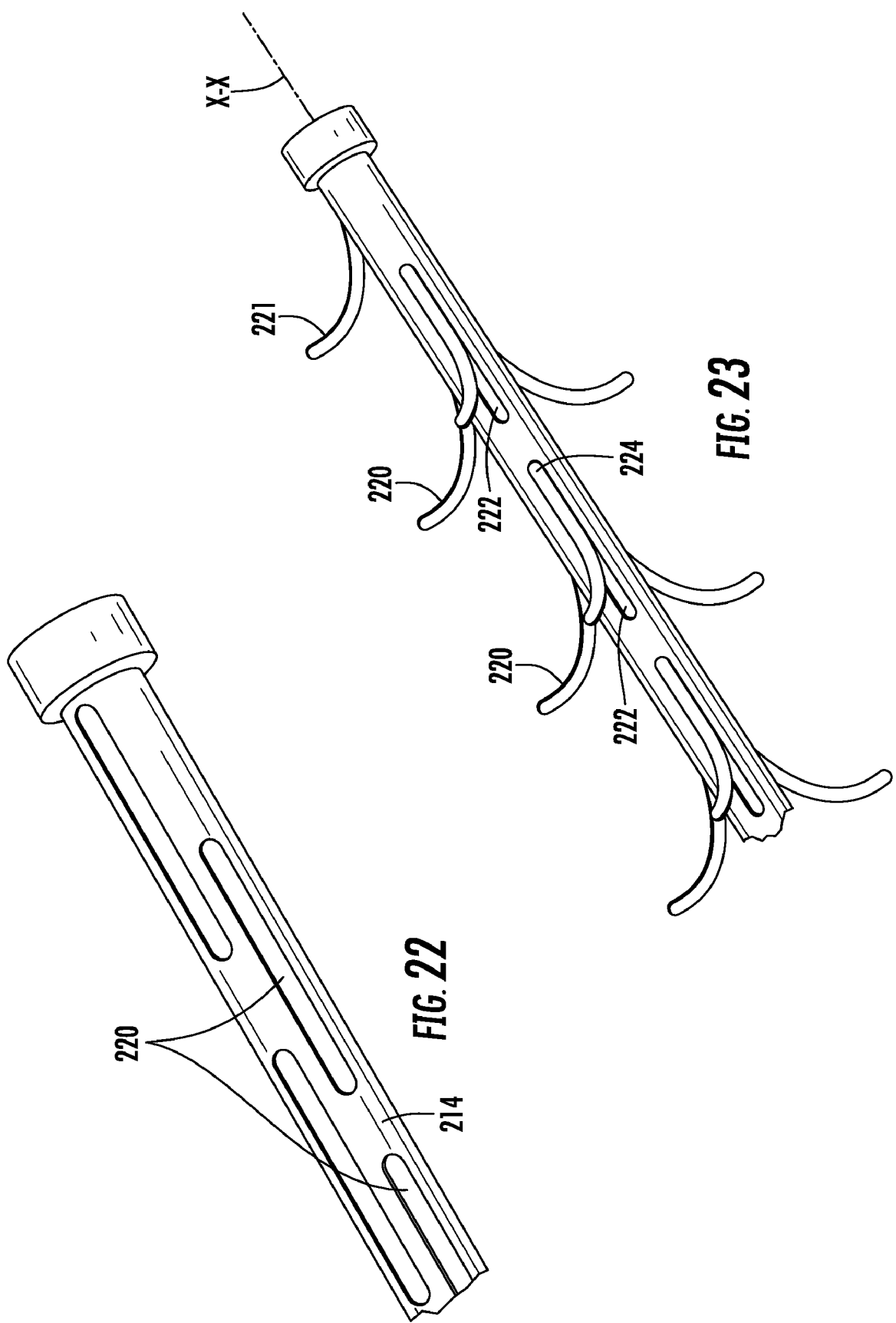

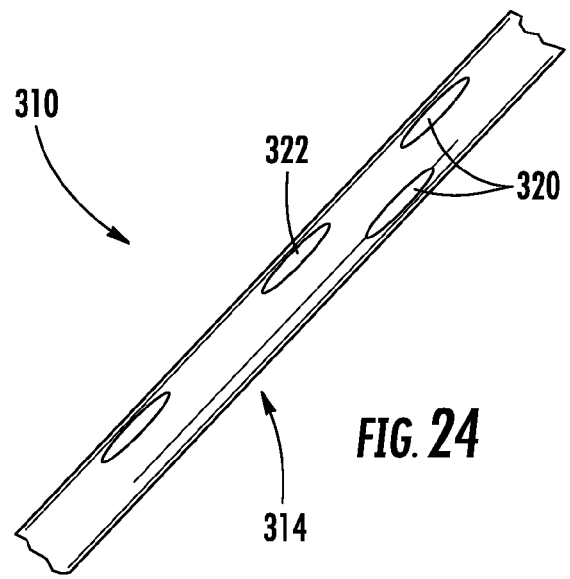
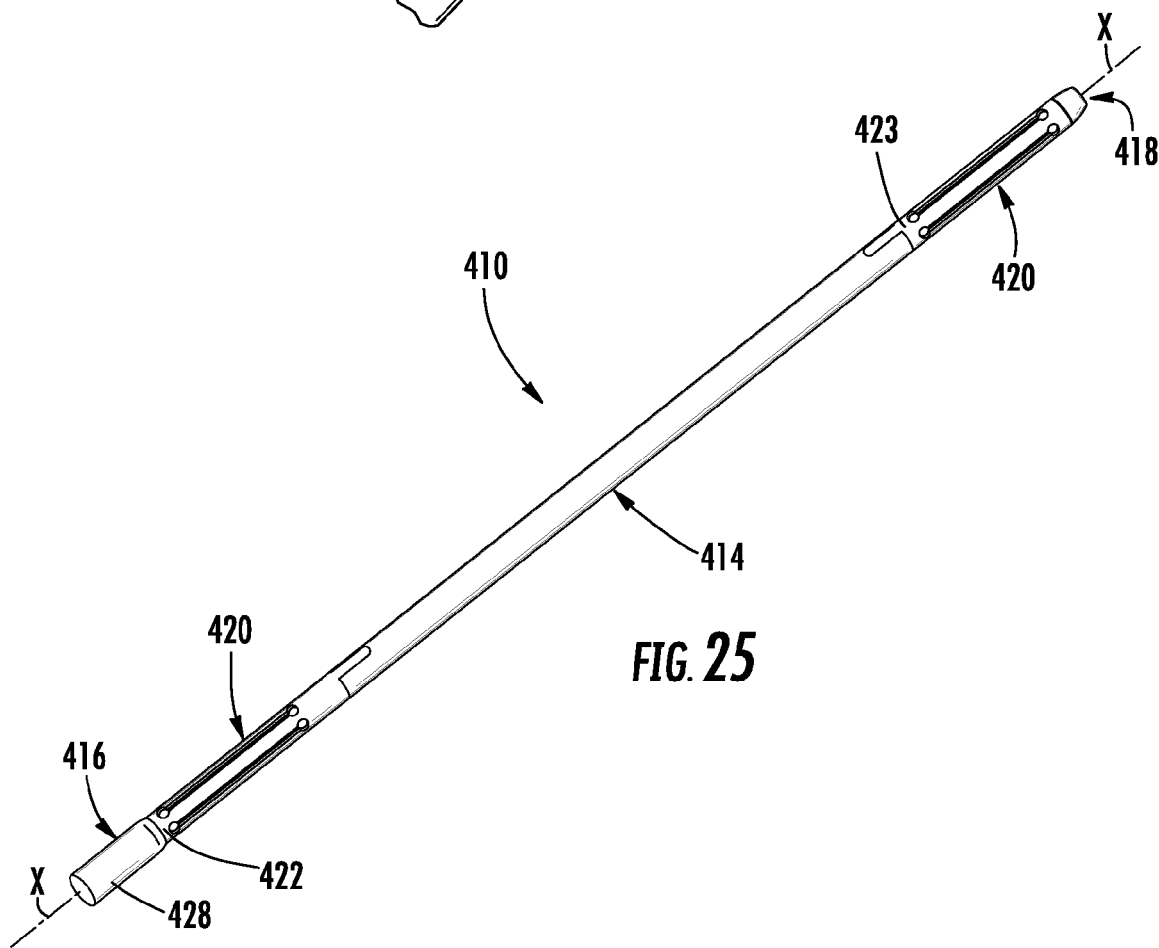

INTRAMEDULLARY NAIL COMPRISING ELEMENTS OF SHAPE-MEMORY MATERIAL

FIELD OF APPLICATION

The present invention relates in its more general aspect to an intramedullary nail suitable for insertion in a fractured elongate bone and an application method of said nail in said bone.

In particular, the invention relates to an intramedullary nail suitable for insertion in a fractured elongate bone, such as a femur or a tibia, comprising a stem extending between a proximal end and a distal end.

PRIOR ART

Intramedullary nails are known, which, during a surgical operation, are inserted in a fractured elongate bone and fixed therein, in order to reconstruct the original bone shape and in the meantime to recover the bone solidity, so that callus regeneration mechanisms can correctly occur.

The stems of these intramedullary nails are generally of substantially cylindrical shape and they can be both solid and hollow.

In order to fix the intramedullary nail to the bone portions to be reconstructed, two or more offset holes are usually provided on the nail, having axes lying on parallel or crossing planes extending diametrically across the stem, in correspondence with the nail distal end, and two or more offset holes having the same size, having axes not necessarily lying on parallel planes, in correspondence with the nail proximal end. Said holes are suitable for housing bone screws, which are inserted, after a convenient bone drilling, in the bone, with the subsequent fixation of the intramedullary nail to the bone portions.

Although advantageous under different points of view, intramedullary nails being structured as above schematically described have known drawbacks mainly occurring when bone drillings are to be performed for bone screw insertion. This step is particularly critical since it is known that a good nail fastening essentially depends on the correct realisation of these bone drillings, obviously made in correspondence with the holes of the inserted intramedullary nail.

However the precise location of the intramedullary nail holes is made difficult by the fact that the holes are no more visible, being the nail inserted in the bone. It is then worth underlining a further location problem, i.e the fact that the intramedullary nail can be, when being inserted, slightly bent, so that the holes at the nail distal end are no more, with respect to the proximal end, in the same position as before installing the nail.

The traditional technique for locating the holes of an inserted intramedullary nail provides the use of X rays, involving however the well known risks of cumulative exposure of the operating staff, besides being quite awkward during the surgical operation.

Specific mechanical devices have thus been studied and realised, such as for example the one described in the European patent no. EP 772 420 in the name of the same Applicant.

These devices do not require the use of X rays, but they have the drawback of requiring several operational steps, all to be performed quite carefully and precisely.

SUMMARY OF THE INVENTION

The problem underlying the present invention is to provide an intramedullary nail suitable for insertion in a fractured elongate bone, capable to meet the above-mentioned requirement, meanwhile overcoming, in a simple and effective way, all the drawbacks mentioned with reference to the prior art.

This problem is solved, according to the present invention, by an intramedullary nail suitable for insertion in a fractured elongate bone, as above described and characterised in that it comprises a plurality of elements realised with at least a shape-memory material and a plurality of seats made in the stem for housing the shape-memory elements.

According to the invention, the shape-memory elements are suitable to take a first shape, or configuration, wherein they are retractably housed in the respective seats of the stem and a second shape or configuration wherein they project from their respective seats.

Further features and the advantages of the intramedullary nail suitable for insertion in a fractured elongate bone, as well as of the application method of said nail in said fractured bone, according to the present invention, will be apparent from the following description of some embodiments thereof made with reference to the attached drawings, given by way of non-limiting example.

BRIEF DESCRIPTION OF THE DRAWINGS

FIGS. 14b-14c shows a section of the nail during an assembly step of the system of FIG. 14a.

FIGS. 15a-15d show a sequence of steps for the insertion of the nail in the bone.

FIG. 16 schematically shows a perspective view of a second embodiment of an intramedullary nail according to the present invention in a first shape or configuration.

FIG. 17 schematically shows a perspective view of the nail of FIG. 16, in a second shape or configuration.

FIG. 18 schematically shows an enlarged perspective view of the nail of FIG. 16.

FIG. 19 schematically shows an enlarged perspective view of the nail of FIG. 17.

FIG. 20 schematically shows a perspective view of a third embodiment of an intramedullary nail according to the present invention in a first shape or configuration.

FIG. 21 schematically shows a perspective view of the nail of FIG. 20, in a second shape or configuration.

FIG. 22 schematically shows an enlarged perspective view of the nail of FIG. 20.

FIG. 23 schematically shows an enlarged perspective view of the nail of FIG. 21.

FIG. 24 schematically shows a partial perspective view of a fourth embodiment of an intramedullary nail according to the present invention in a first shape or configuration.

FIG. 25 schematically shows a perspective view of a fifth embodiment of an intramedullary nail, suitable for insertion in a fractured elongate bone, according to the present invention in a first shape or configuration.

DETAILED DESCRIPTION

Figure 1:
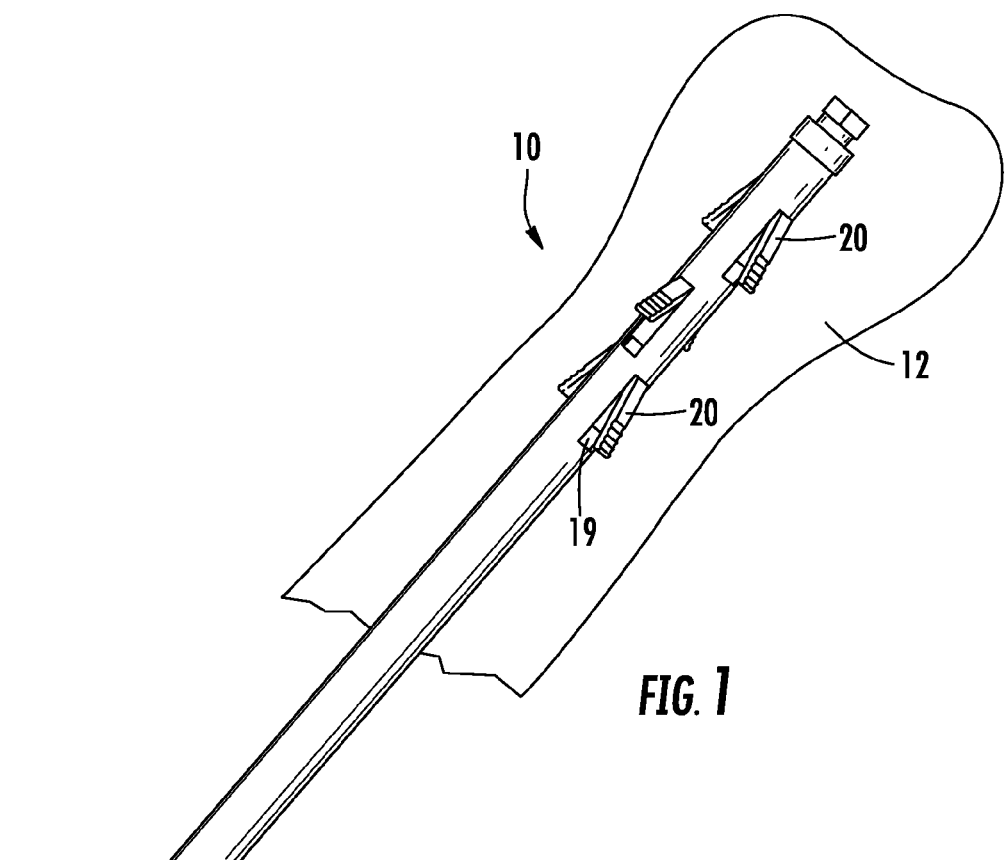
FIG. 1 schematically shows a perspective view of a nail according to the present invention in accordance with a first embodiment and provided with a sheathing tubular jacket or sheath.
Figure 2:
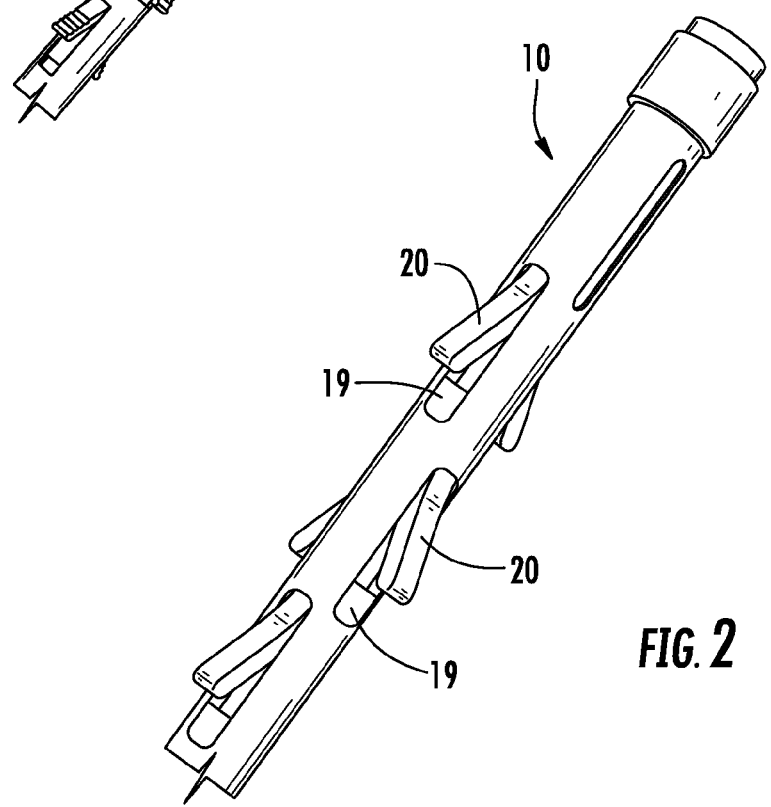
FIG. 2 shows a partial view of the nail of FIG. 1, wherein the shape-memory elements take a first shape or configuration.
Figure 3:
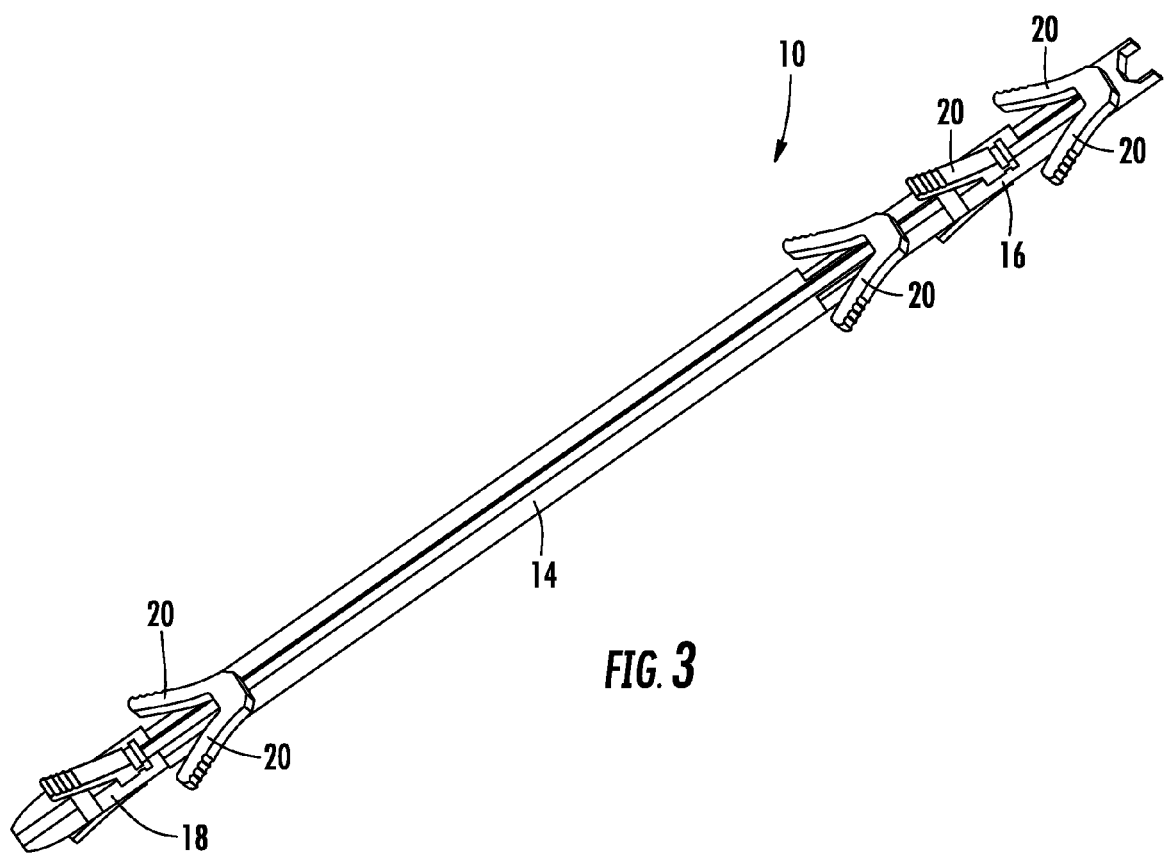
FIG. 3 shows a section view of the nail of FIG. 1 devoid of the sheathing tubular jacket of FIG. 1.
Figure 4:
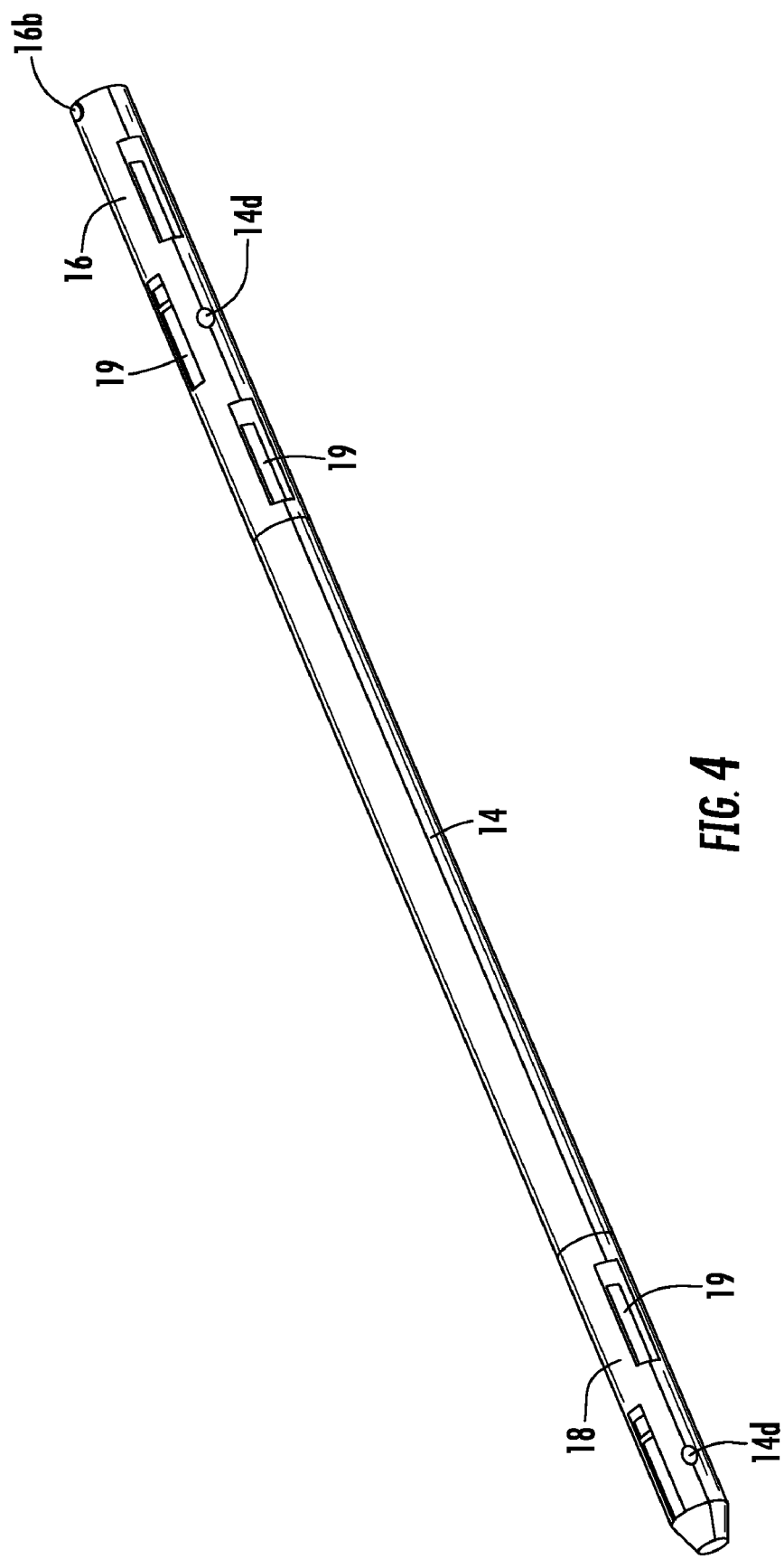
FIG. 4 shows a stem of the nail of FIG. 1.

Referring first to FIGS. 1-15, an intramedullary nail according to the present invention is shown and globally indicated with 10, suitable for insertion in a fractured elongate bone 12, such as for example a femur or a tibia.

The nail 10 comprises a stem 14 extending between a proximal end 16 and a distal end 18.

The stem 14 is preferably composed of a cylindrical tubular body. The stem 14, according to an aspect of the present invention, comprises a plurality of elements 20 realised with at least a shape-memory material and a plurality of seats 19 formed in the stem 14 for housing the elements 20.

The elements 20 are preferably similar to each other.

The elements 20 are suitable to take a first shape, or configuration, wherein said elements 20 are retractably housed in the respective seats 19, so as to allow the insertion of the nail in the bone and a second shape or configuration wherein said elements 20 are projecting from the respective seats 19 for allowing the grip and the fixing in the fractured bone.

Shape memory material means a material, already known in the technique, having a given starting shape and taking, under predetermined external conditions or undergoing a predetermined activation condition, after a so-called "material instruction" step, a given new shape.

Within the present invention, the starting shape corresponds to the second shape or configuration wherein the shape-memory elements are arranged projecting form the stem.

Preferably, the new shape, or first shape, is taken by lowering the temperature of the nail.

Within the present invention, this new shape corresponds to the above first shape, or configuration, which is taken by the shape-memory elements 20 retractably arranged in the seats 19 of the nail 10.

Under such condition, the nail 10 can be inserted in the bone.

When the activation condition fails, for example in case of temperature increase, the shape-memory elements 20 take the starting shape again.

As above anticipated, within the present invention, the starting shape is the above second shape or configuration, wherein the nail is fixed to the bone by means of the elements 20 projecting from the stem 14.

The particular characteristic of the shape-memory elements stays in that the taking of the second shape or configuration, i.e. the return to the starting shape, under determined physical conditions, continues until the "memorised" starting shape is reached.

This characteristic ensures a constant push, or thrust, into the bone, also in case the bone should be reabsorbed for any reason losing its original shape and size.

The expansion temperature of the shape-memory elements from the first to the second shape or configuration can be obtained by means of the body temperature in case a shape-memory material having a so called Af (i.e. end point of the transition while heating), which is lower than, or equal to, 37° C. (e.g. 25° C.) is used. In case of shape-memory materials having an Af around 48° C. suitable heating tools are used.

Another characteristic of the shape-memory material stays in that the transition from the first to the second shape, or configuration, is reversible, i.e. the shape-memory elements can be transformed from the second to the first shape, or configuration, allowing the extraction of the nail from the bone.

Making now reference to FIGS. 1-15, a first embodiment of an intramedullary nail according to the present invention and globally indicated with 10 is shown, suitable for insertion in a fractured elongate bone 12. In such embodiment, the nail 10 comprises a stem 14 having a diameter preferably in the range of 7 to 12 mm.

In a head portion of the stem 14 a threading 16a is made (FIG. 9) for a threaded connection with a suitable driving tool 13 for gripping the nail. For maintaining the threaded connection in phase with the driving tool 13, grooves 16b are also present.

The connection of the nail 10 with the grip driving tool will be better explained hereafter with reference to FIGS. 14a-14d and 15a-15d.

For facilitating the insertion of the nail 10 in the bone, the tip portion of the stem 14 is preferably rounded so as to allow a sliding of the nail in the medullary channel.

In the case of the shown solution, the stem 14 is substantially straight. However, according to the anatomic needs of the elongate bone, the stem 14 can be curved, or bent so that the proximal end 16 forms angle with the distal end 18.

The stem 14 is also of the cannulated type and it is preferably made of a cylindrical tubular body. The stem 14 is also provided with transversal holes 14d for the insertion of pins suitable to avoid a torsion of the nail in the bone.

The stem 14, according to an aspect of the present invention, comprises a plurality of transversal slots 19, or elongate holes, also called openings, which extend passing from one side of the stem 14 to the other. The slots 19 serve as seat for housing the shape-memory elements 20.

More precisely, and as it is possible to see from the figures, since the stem 14 is cannulated, each transversal slot 19 forms a pair of elongate holes which are realised on opposite walls of the stem 14. For simplifying the illustration, here and in the rest of the description, these opposite elongate holes will be considered as a single transversal slot 19 (FIG. 7), which defines the seat where a corresponding element 20 realised with shape-memory material is housed.

In the example of FIGS. 1-15 the shape-memory elements 20 form inserts 23, structurally independent from the stem 14, and suitable to be inserted in the transversal slots 19. Preferably, in the case of the illustrative solution, for facilitating the insertion of the inserts 23, the stem 14 is made of two united half-cylinders, for example welded, along the length.

The inserts 23 are preferably inserted fixedly or by pressure in the respective slots 19.

In particular, each insert 23 comprises a pair of elements 20. For forming each insert 23, the elements 20 forming the above pair are connected to each other by means of a connection central element 22.

An insert 23 is thus obtained having substantially fork-like shape. Preferably, the fork is symmetrical and it has an upturned V or U-like shape. The symmetry of the fork allows to obtain a balanced push onto the bone.

The fork-like insert 23 is suitable to be housed in the corresponding transversal slot 19, so that the two elements 20 forming the above pair are arranged on the opposite sides of the stem 14.

In this way, on the surface of the stem 14 there are a plurality of inserts 23, inserted in the respective slots 19 and flanked in succession along the length, wherein each insert 23 is provided with two shape-memory elements 20.

Preferably, the plurality of inserts 23 is distributed on the side surface of the stem 14 in correspondence with the proximal end 16 and with the distal end 18. In this way the central portion of the stem 14 has a substantially smooth surface.

In the case of the shown solution, the distal portion 18 comprises two inserts 23, whereas the proximal portion 16 comprises three inserts 23.

Always preferably in the above succession, the inserts 23 are arranged as offset with one another, for example they are arranged with a offset of sexagesimal 90°. The offset arrangement ensures a determined stability on orthogonal planes.

Figure 5:
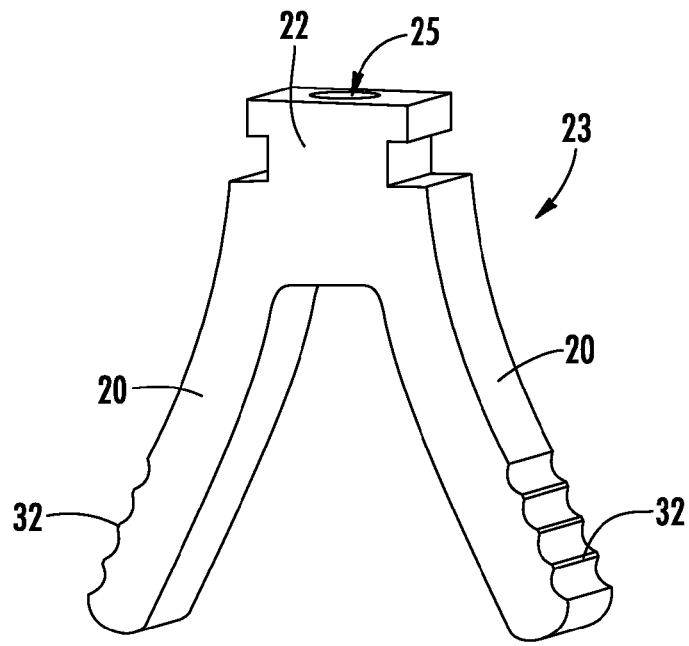
FIG. 5 shows a view of an insert comprising shape-memory elements for the nail of FIG. 1.
Figure 6:
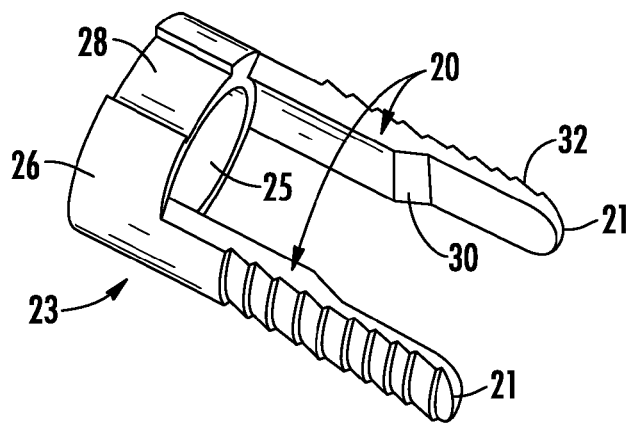
FIG. 6 shows a view of an insert comprising shape-memory elements according to a further embodiment.
Figure 7:
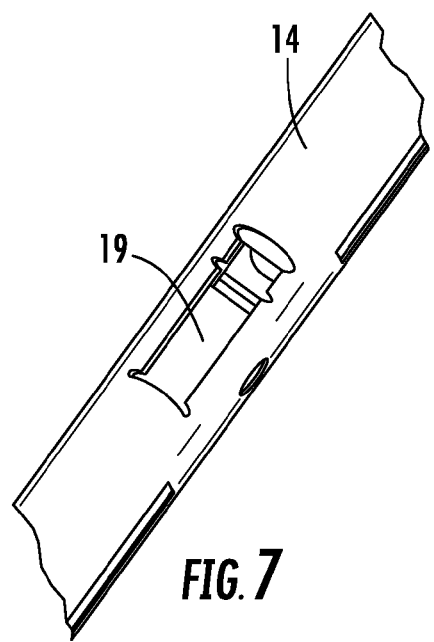
FIG. 7 shows a view of an enlarged portion of the stem of FIG. 4.
Figure 8:
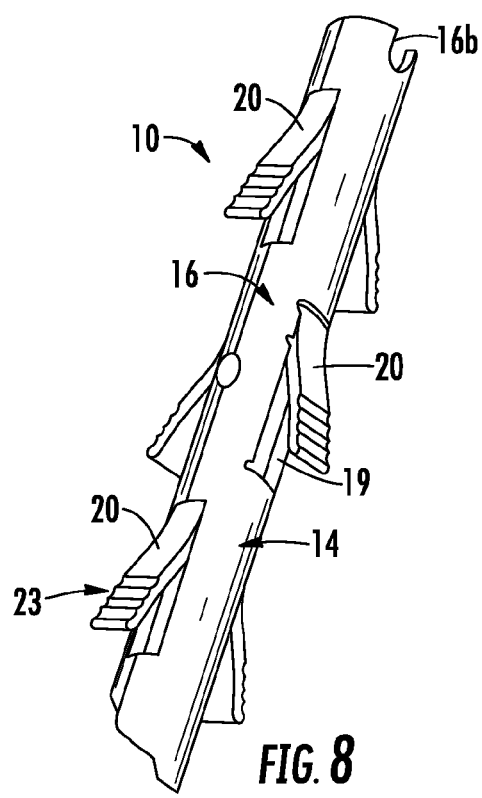
FIG. 8 shows a view of an enlarged portion of the nail of FIG. 1 provided with shape-memory elements.
Figure 9:
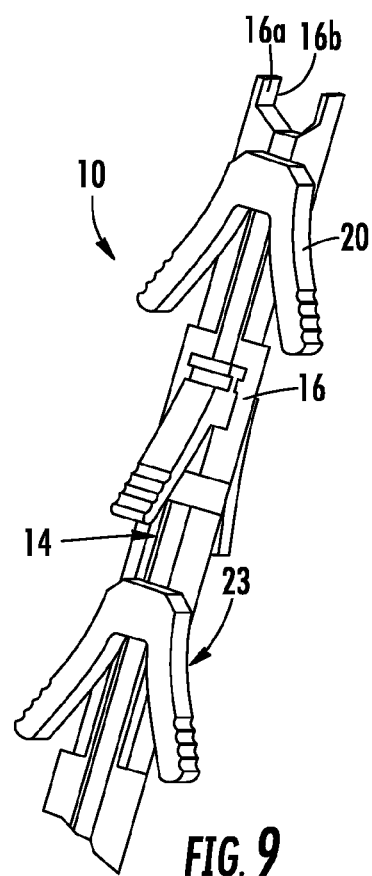
FIG. 9 shows a section view of the portion of the nail of FIG. 8.
Figure 10:
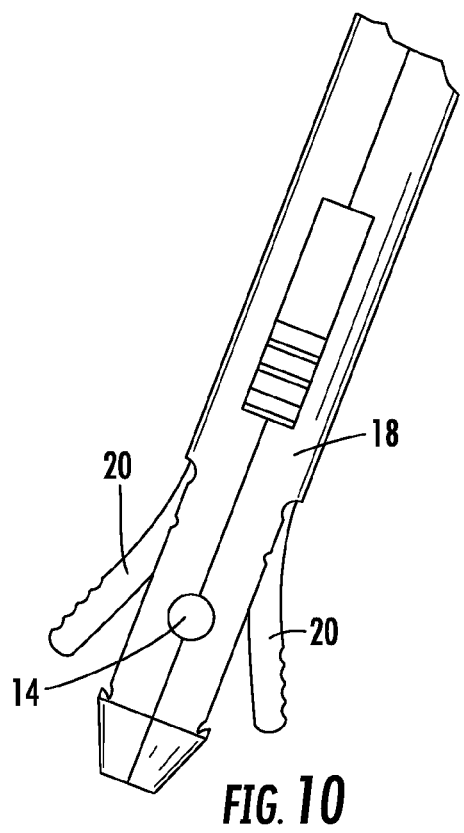
FIG. 10 shows a view of the enlarged end portion of the nail of FIG. 1 provided with shape-memory elements.
Figure 11:
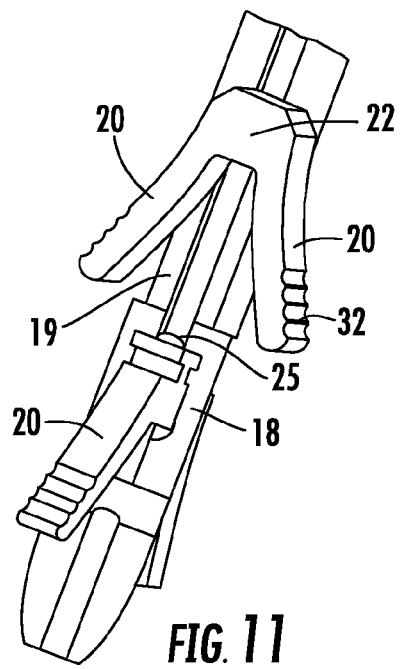
FIG. 11 shows a section view of the portion of the nail of FIG. 10.
Figures 12, 13:
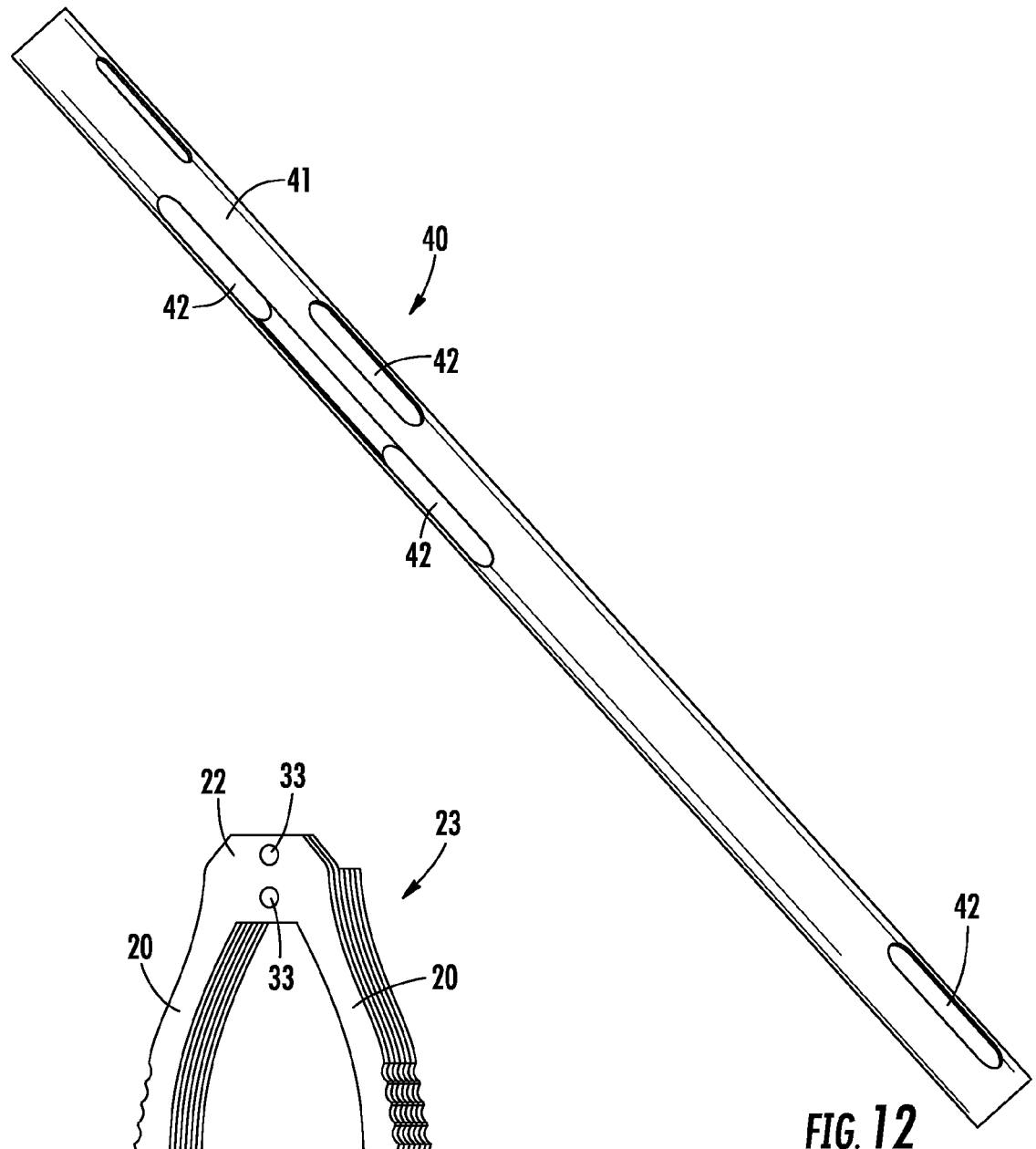
FIG. 12 shows a view of the tubular jacket for sheathing the nail of FIG. 1.
FIG. 13 shows a view of an insert comprising shape-memory elements according to a further embodiment.

With reference to FIGS. 5, 6 and 13, the two elements 20 forming the pair of each insert 23 consist of two opposite elongate tabs or fillets 20. According to the invention, when the nail 10 is in the first shape or configuration and is inserted in the bone, the tabs 20 are substantially aligned with the connection body 22 so as to retractably lie in the slots 19.

When the nail is completely inserted in the bone and it is in the second shape or configuration, the tabs 20 are wide apart with respect to the connection body 22 so that the free ends 21 of the tabs 20 are projecting from the slots 19.

In other words, the tabs 20 have a flexural memory.

Preferably, in the case of the insert 23 of FIG. 5, the tabs 20 have a thickness equal to the connection body 22, so as to obtain an insert 23 having a uniform thickness.

The tabs 20, on the surface facing outwards from the stem 14, also have a substantially sawtooth-like profile 32 for improving the grip of the tab 20 with the bone.

The length of the tabs 20 can vary according to the position of the nail with respect to the distal 18 or proximal 16 portion, and according to the treated bone.

In the femur, for example, for better responding to the anatomy, the tabs 20, in the distal portion 18, nearer the tip of the nail 10 and, respectively in the proximal portion 16, nearer the head of the nail 10, are longer than the tabs arranged in the central area of the stem 14.

As it is possible to observe from the drawings, also the insert 23 is provided with a hole 25 on the connection body 22. The hole 25 is coaxial to the axial hole of the stem 14 and it allows the insertion of a guide wire, such as for example a Kirschner wire.

According to a further embodiment, shown in FIG. 13, each insert 23 is of the multilaminar type, i.e. it is realised by means of a plurality of metallic foils being overlapped and welded one on the other.

In this case, for ensuring a stable assembly of the metallic foils, the insert 23 is provided with a pair of blocking pins 33 inserted transversally to the metallic foils. Preferably, the use of blocking pins is provided also for tidying the insert 23 on the stem 14 once it is arranged inside the seat 19.

According to a further embodiment shown in FIG. 6, the nail 10 comprises, as connection element, a cylindrical sleeve 26 for the connection with the two shape-memory elements 20.

In the case of the solution shown in FIG. 6, two opposite grooves 28 are also provided on the cylindrical sleeve 26, being substantially offset of a straight angle with respect to said two tabs 20 and suitable to house at least partially the tabs of a cylinder 26 flanked along the stem axis. In this way, the sleeves 32 are overlapped with respect to each other.

In this embodiment of FIG. 6, the profile of the tabs 20 is tapered towards the free end 21.

In particular, on the tab surface facing the stem 14, a section is provided with an inclined surface 30 which leads to a thinning of the tab thickness in correspondence with the section towards the free end 21.

According to another characteristic of the present invention, the nail 10 comprises a sheathing tubular jacket 40 (FIGS. 12, 14, 15a-15d) wherein the stem 14 is inserted. For simplicity of illustration, the sheathing jacket 40 is described with reference to the nail 10 of FIGS. 1-15, however it is clear that such jacket 40 can be also used for the nails of the hereafter described embodiments.

Figure 14:
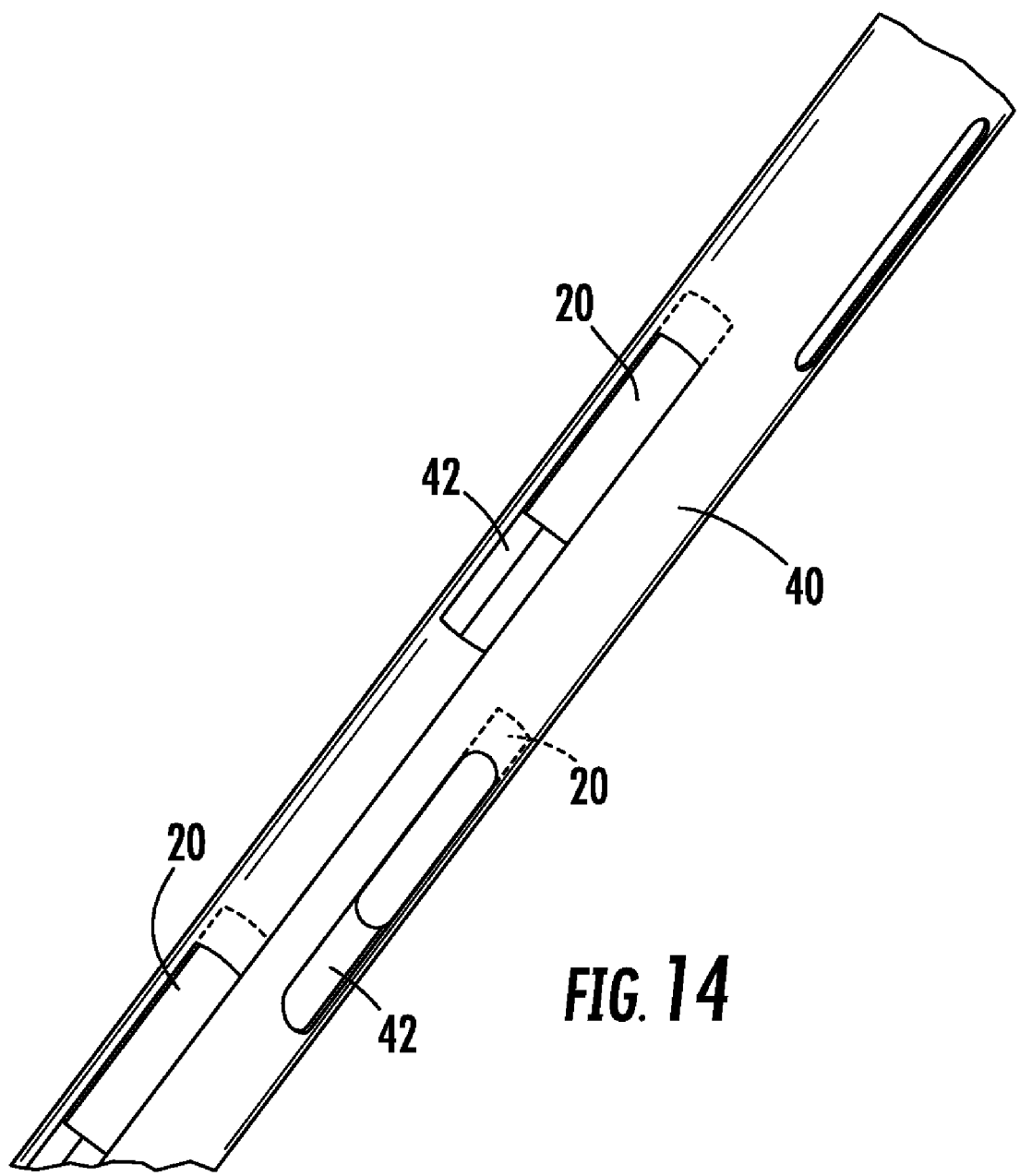
FIG. 14 shows a detail of a head portion of the nail of FIG. 1 wherein the shape-memory elements take a first shape or configuration.

The jacket 40 has a substantially tubular shape and it has the function of retaining, according to the need, the shape-memory elements 20 in the first shape, i.e. in the closed retractable position in the slots 19, as shown in FIG. 14.

In other words, the jacket 40 allows to firmly maintain the shape-memory elements 20 in the seats 19, before the nail 10 is inserted in the bone and until it is inserted in the medullary channel.

The jacket 40 particularly comprises a side wall 41 and a plurality of transversal elongate holes 42, made in the tubular wall 41.

According to a characteristic of the invention, the jacket 40 and the stem 14 can be shifted with respect to each other between a first operative position during which the side wall 41 closes at least partially the shape-memory elements 20 in the first retractable shape in the seats 19, and a second operative position wherein the transversal elongate holes 42 of the jacket 40 are aligned with the slots 19 of the stem 14, so as to allow the taking of the second shape by the elements 20, and thus their widening apart outside the slots 19.

Preferably, the shift relative to the jacket 40 with respect to the stem 14 occurs along the axis of the nail 10.

Preferably, the above shift is obtained by means of a suitable driving tool. In particular, the driving tool is configured to shift the stem 14 with respect to the jacket 40.

Figure 14A:
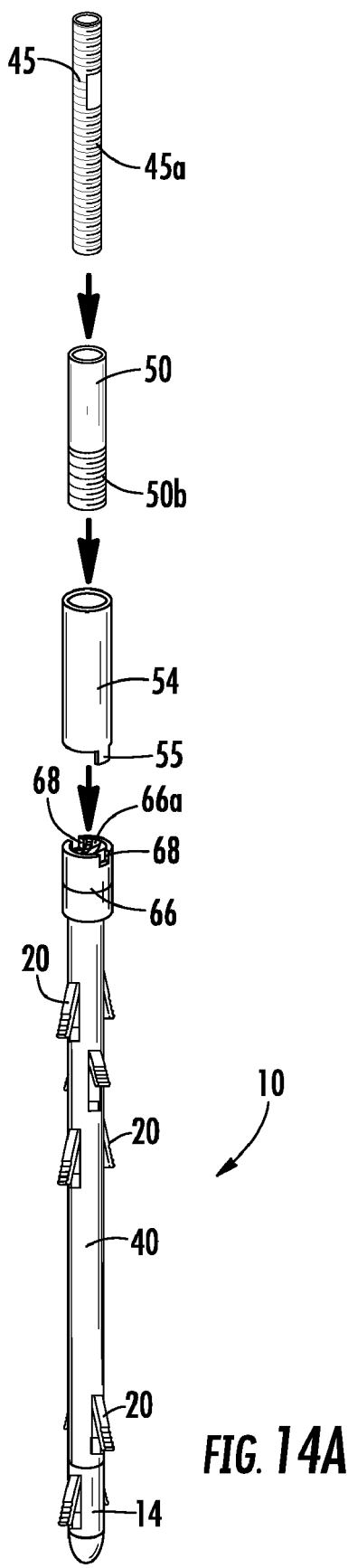
FIG. 14a shows an exploded view of a system for shifting the nail of FIG. 1.
Figure 14B:
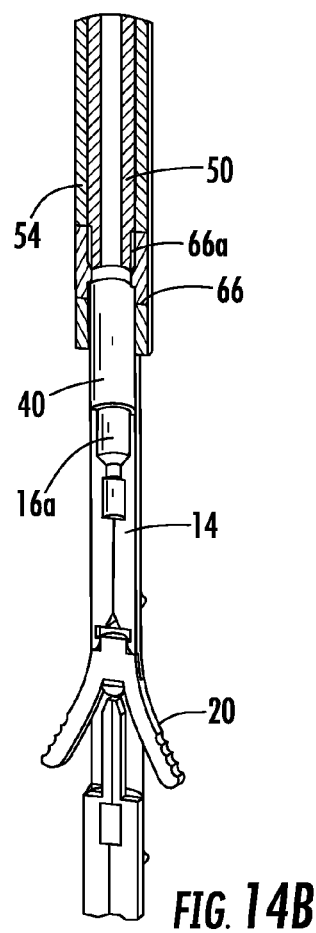

To do this, the nail 10 is provided with a so called double-threading system (FIGS. 14a and 14b).

A first threading in the above-mentioned threading 16a of the nail 10 head. In this first threading 16a a control screw 45 (FIG. 14c) provided with relative threading 45a is intended to be screwed.

A second threading 66a is made in a cylindrical body 66 (FIGS. 14a and 14b) welded on the head portion of the jacket 40.

The cylindrical body 66 is provided with a pair of recesses 68, which are intended to receive corresponding teeth 55 of a bearing sleeve 54. The bearing sleeve 54 allows to maintain the jacket 40 axially firm during the shift of the nail 10.

In the threading 66a of the cylindrical body 66 a tube 50 provided with relative threading 50b is screwed, being inserted in the bearing sleeve 54. The tube 50 is internally hollow to blacklash-like house inside the above control screw 45.

In particular, FIG. 14B shows the tube 50 housed in the bearing sleeve 54a and firmly screwed in the second threading 66a.

Figure 14C:
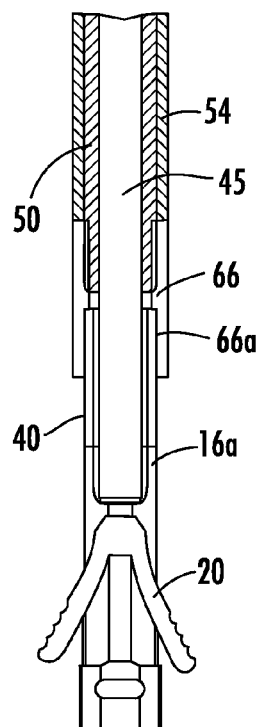
Figure 14D:
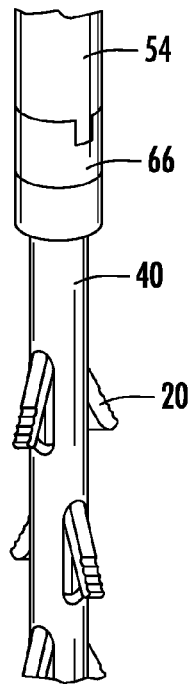
FIG. 14d shows a partial view of the nail according to the invention.
Figure 26:
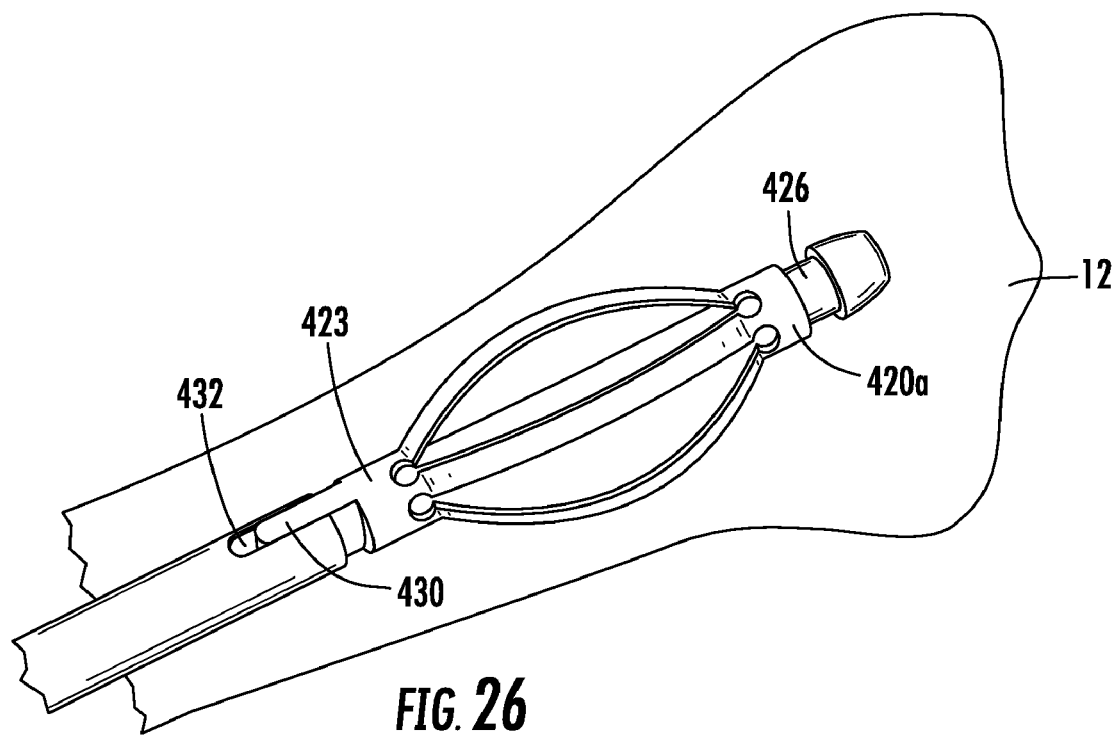
FIG. 26 schematically shows an enlarged perspective view of the nail of FIG. 25 in a second shape or configuration.
Figure 27:
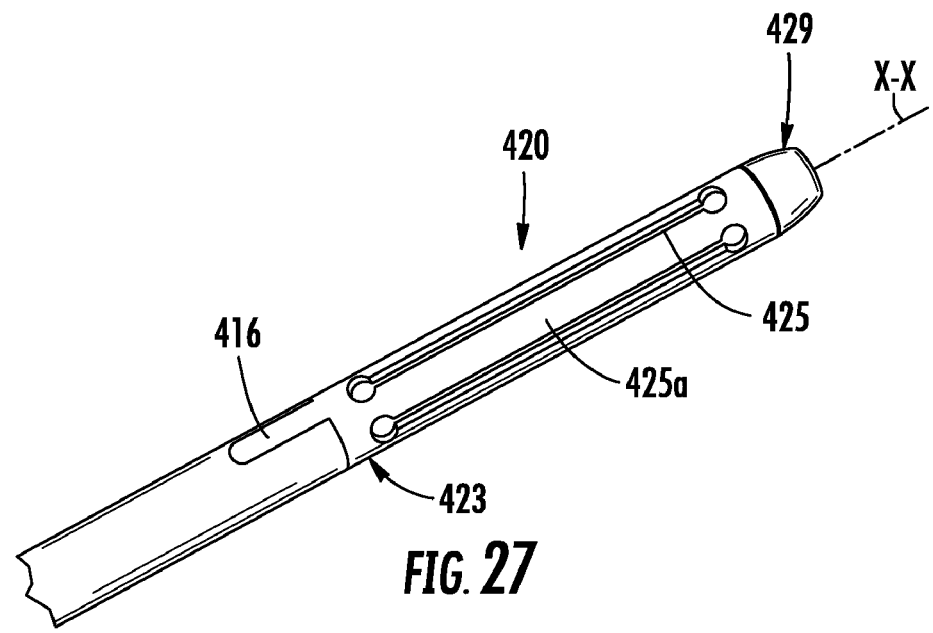
FIG. 27 schematically shows a perspective view of the nail of FIG. 26, in a first shape or configuration.
Figure 28:
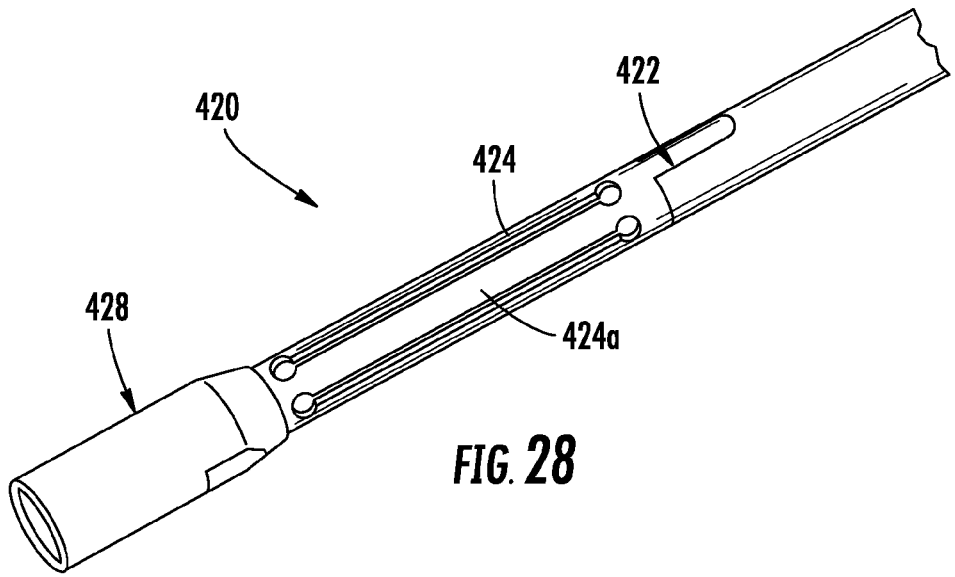
FIG. 28 schematically shows a further enlarged perspective view of the nail of FIG. 25.
Figure 29:
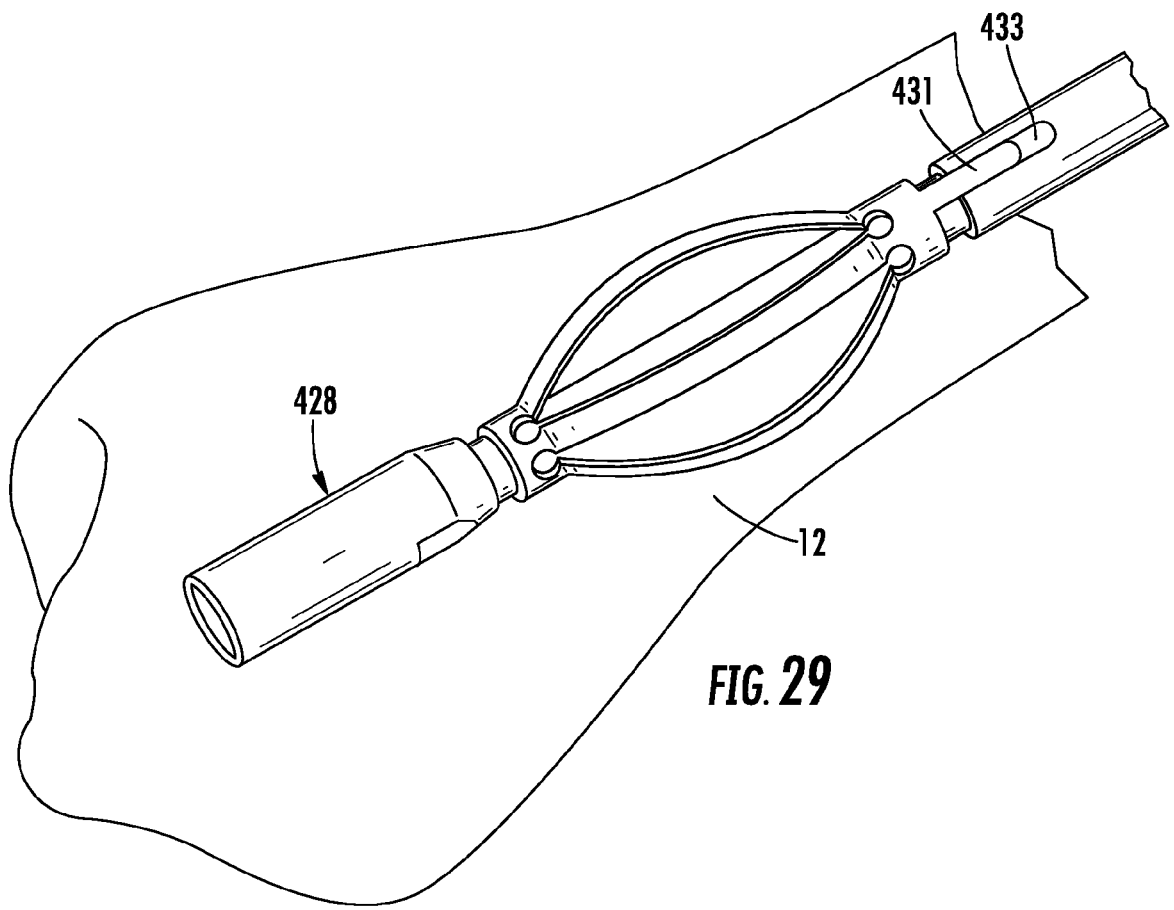
FIG. 29 schematically shows a perspective view of the nail of FIG. 26, in a second shape or configuration.
Figure 30:
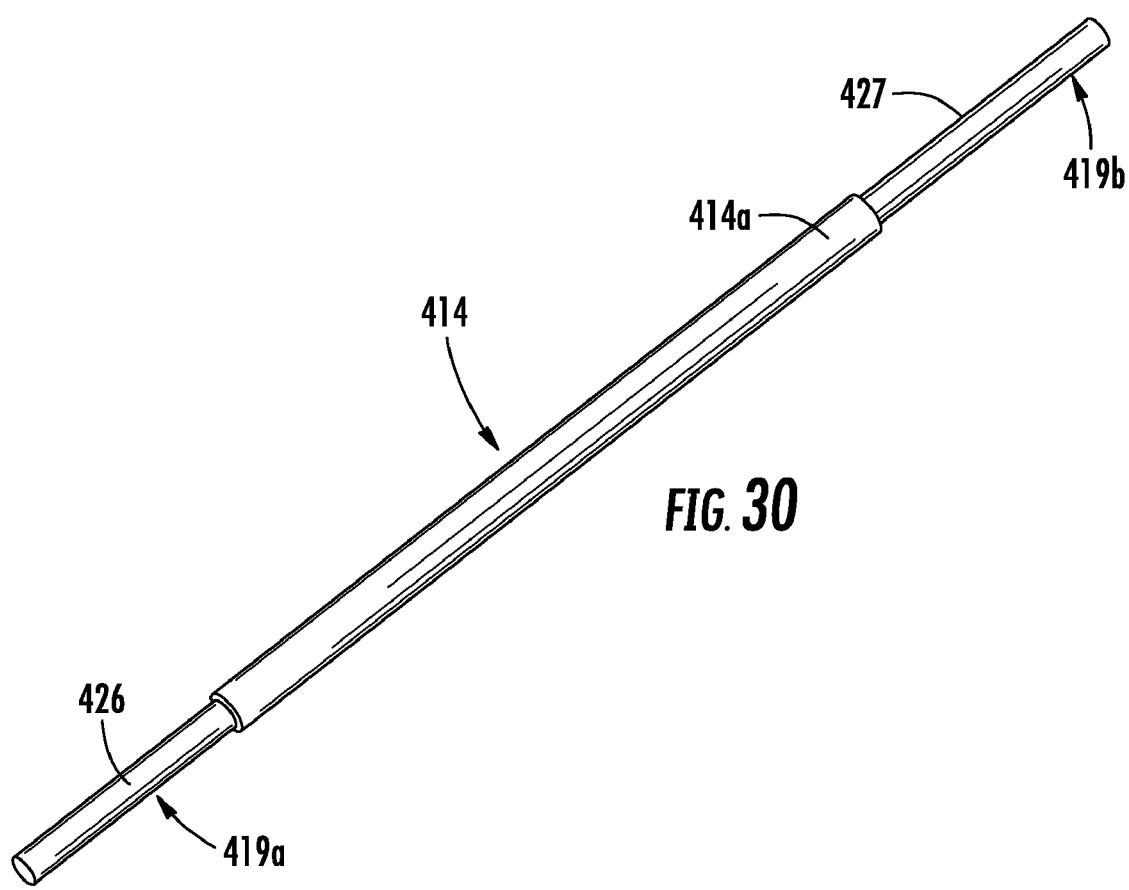
FIG. 30 schematically shows a perspective view of a portion of the nail of FIG. 25.

FIG. 14C shows the control screw 45 inserted in the tube 50 and firmly screwed in the first threading 16a of the nail 10.

To determine an axial reciprocating shift of the nail 10 with respect to the jacket 40 it is enough to rotate the control screw 45 in a sense, or in the other, around its own axis with respect to the tube 50.

In the case of the shown solution, a clockwise rotation of the control screw 45 determines a setting back of the nail 10 (FIG. 15a), whereas a counter-clockwise rotation causes an advance of the nail 10 (FIG. 15b).

With reference to FIGS. 15a-15d the application of the nail 10 in a bone 12 is now described.

Starting from the condition shown in FIG. 15a, wherein the elements 20 are in the starting shape (second shape or configuration), the control screw 45 is screwed, for example clockwise, determining an axial setting back of this latter (FIG. 15a).

As above described, the jacket 40 is firmly kept by the bearing body 54 and by the tube 50.

Due to the axial shift of the nail 10, a portion of the side wall 41 of the jacket 40 partially closes the slot 19 of the stem 14 (FIG. 14). In this way the jacket wall presses the tab 20 facilitating the taking of the first shape or configuration, i.e. wherein the elements retractably lie in the slots.

This operation is performed when the nail is at low temperatures and the material is instructed to take the first shape or configuration (FIG. 15b).

At this point, the nail 10, thus arranged, is inserted in the nail (FIG. 15c).

Once the nail 10 is inserted in the bone, the tabs 20 can be freed from the tie exerted by the jacket 40 for allowing to take of the second shape or configuration, i.e. the one projecting from the slots 19 (FIG. 15d).

To do this, the control screw 45 is rotated counter-clockwise with respect to the tube 50. In so doing the nail 10 is axially advanced with respect to the jacket 40, until a complete alignment of the elongate holes 41 and of the slots 19 of the nail is obtained.

In such position, the tie of the wall 42 on the tabs 20 fails, allowing a free widening apart of the ends 21 of the tabs 20.

Once the nail is inserted in the bone 12, the bearing body 54, the tube 50 and the control screw 45 can be removed.

The method described up to now can be performed in an inverted way during an extraction step of the nail 10 from the bone.

In such case, when the nail 10 is in the bone, the inserts 23 can be cooled for example, by inserting a cooling element in the stem, so as to allow the retractably positioning of the elements 20 in the seats 19.

Under such condition, the bearing body 54, the tube 50 and the control screw 45 are applied again on the nail and the control screw 45 is rotated clockwise, so as to make the nail 10 set back and to tie the elements 20 by means of the jacket 40.

Under such condition, the nail 10 can be removed from the bone with a minimum invasiveness.

With reference to FIGS. 16-34 further embodiments of the nail according to the present invention are now described.

In the embodiment of FIGS. 16-19, each shape-memory element 120 is housed in a corresponding groove 122, with function of housing seat 119, which circumferentially develops along the side surface of the stem 114, said groove 122 generally having a U-shaped profile.

The element 120 has the shape of a sector of a cylindrical crown and its thickness is substantially equal to the depth of the groove 122. Such element 120 is fixed, for example through laser welding or keying, along its side end 124 (which substantially develops along the axis of the stem 114) in the groove 122.

The above description corresponds to the first shape of the element 120. In the final second shape, leading to the fixation of the nail 110 to said fractured bone 12, the free end 121 of the element 120, being the opposite end to said side end 124, projects from the groove 122: for example, the sector of a cylindrical crown of the initial shape straightens, substantially becoming a parallelepiped.

Preferably, in the series of grooves 122, the elements 120, all having the same angular development, are offset to each other. In the example of the figures, three further elements arranged in different angular positions exist between two elements 120 arranged in the same angular position.

Moreover, always preferably, the side ends 124 wherein each element 120 is fixed are, in the series of grooves 122, alternate to each other i.e., observing the stem 114 in the vertical position, at one time the side end 124 is on the left and next time it is on the right.

The stem 114 can be connected with an outer template by means of a side thread.

It must be observed that the circumferentially-developing grooves 122 can be realised along the whole circumference or they can be developed only along the circumference arc corresponding to the cylindrical crown sector of the elements 120.

Referring now to FIGS. 20, 21, 22, 23, a third embodiment of the intramedullary nail, according to the present invention is shown and globally indicated with 210, suitable for insertion in a fractured elongate bone 12.

The nail 210 comprises a substantially straight stem 214 extending between a proximal end 216 and a distal end 218.

The stem 214 is preferably composed of a cylindrical tubular body. The stem 214, according to an aspect of the present invention, comprises a plurality of elements 220 realised with at least a shape-memory material of the above-described type.

Preferably, the plurality of elements 220 are distributed in a substantially uniform way on the side surface of the stem 214.

In particular, in the example of FIG. 20, each element 220 is housed in a corresponding groove 222 defining the above housing seat 219 axially developing along the side surface of the stem 214, said groove 222 generally having a U-shaped profile.

The element 220 is cylinder-shaped and the thickness thereof is substantially equal to the depth of the groove 222. This element 220 is fixed in the groove 222, (for example by laser welding) in correspondence with the front end 224 thereof.

The above description corresponds to the first shape of the element 220. In the final second shape, leading to the fixation of the nail 210 to said fractured bone 12, the free end 221 of the element 220, being the opposite end to said front end 224, projects from the groove 222: for example, the straight-developing cylinder of the initial shape bends outwards the stem 214, taking thus a curvilinear development.

Preferably, in the series of grooves 222, the elements 220, all having the same length, are arranged with the front ends 224 being offset to each other. In the example of the figures, two further elements arranged with the front ends 224 in different angular positions exist between the front ends 224 of two elements 220 arranged in the same angular position.

Moreover, always preferably, the front ends 224 wherein the elements 220 are fixed are all those turned towards a same end (proximal 216 or distal 218) of the nail 210: this serves to facilitate a possible extraction of the nail 210.

The stem 214 can be connected with an outer template by means of a side thread.

Referring now to FIG. 24, a fourth embodiment of the intramedullary nail, according to the present invention is shown and globally indicated with 310, suitable for insertion in a fractured elongate bone 12.

The nail 310 comprises a substantially straight stem 314 extending between a proximal end and a distal end.

The stem 314 is preferably composed of a cylindrical tubular body. The stem 314, according to an aspect of the present invention, comprises a plurality of elements 320 realised with at least a shape-memory material.

Preferably, the plurality of elements 320 are distributed in a substantially uniform way on the side surface of the stem 314.

In particular, in the example of FIG. 24, each element 320 is housed in a corresponding groove 322 with function of housing seat axially developing along the side surface of the stem 314.

The thickness of the element 320 is substantially equal to the depth of the groove 322, said element 320 being fixed in the groove 322, (for example by laser welding) in correspondence with a bottom thereof.

Making now reference to FIGS. 25-30 a fifth embodiment of a nail 410 according to the invention is now described.

In this case, shape-memory elements 420 are provided in correspondence with each one of the two proximal and distal ends 416 and 418 of the nail.

In particular, a first element 420a realised with a memory material arranged at the proximal end 416 materialises into a first cylindrical sleeve 422, preferably equipped with a plurality of longitudinal slots 424 (in the shown example they are four). They are angularly equally spaced around the cylinder of the first sleeve 422, the slots 424 defining a plurality of fillets 424a. The slots 424, at the two opposite longitudinal ends, are shaped according to a circumference arc.

The cylindrical tube of the stem 414 has, in correspondence with the proximal end 416, a first narrow section 426, around which the first sleeve 422 is worn. As it is possible to observe from FIG. 30, the first narrow section 426 defines a first housing seat 419a for the shape memory elements 420a.

The first narrow section 426 has a thread (not shown in the figures) at the stem free end, a retaining ring 428 of the cylindrical sleeve 422 being screwed on said thread, defining a position of the first sleeve 422 with respect to said first narrow section 426.

Moreover, the first sleeve 422 comprises at least one tongue-shaped appendix 430 extending, in a longitudinal direction, towards a stem central portion 414a: the appendix 430 is housed in a corresponding tongue housing 432 provided on the stem and starting from the end of the first narrow section 426 opposite to said free end. Therefore a relative-rotation-free coupling is ensured between the first sleeve 422 and the stem 414.

A second element 420a realised with a shape-memory material arranged at the distal end 418 consists of a second cylindrical sleeve 423, preferably equipped with a plurality of longitudinal slots 425 (in the shown example they are four). They are angularly equally spaced around the cylinder of the second sleeve 423, the slots 425 defining a plurality of fillets 425a. The slots 425, at the two opposite longitudinal ends, are shaped according to a circumference arc.

The cylindrical tube of the stem 414 has, in correspondence with the distal end 418, a second narrow section 427, around which the second sleeve 423 is worn. Also in this case, the second narrow section 427 defines a second housing seat 419b for the shape memory element 420b.

The second narrow section 427 has a thread (not shown in the figures) at the stem free end, a retaining plug 429 of the cylindrical sleeve 423 being screwed on said thread, defining a position of the second sleeve 423 with respect to said second narrow section 427.

Similarly to the first sleeve 422, the second sleeve 423 comprises at least one tongue-shaped appendix 431 extending, in a longitudinal direction, towards a central portion 414a of the stem: the appendix 431 is housed in a corresponding tongue housing 433 provided on the stem central portion 414a and starting from the end of the second narrow section 427 opposite to said free end. Therefore a relative-rotation-free coupling is ensured between the second sleeve 423 and the stem 414.

The first sleeve 422 and the second sleeve 423 are similar and they are specularly positioned, with the stem tongue housing 432 being angularly positioned in correspondence with the stem tongue housing 433.

The above description corresponds to the initial shape, or first shape, of the shape-memory elements 420, wherein the elements 420 are retractably housed in the relative seats 419a, 419b.

In the final shape, corresponding to the fixation of the nail 410 to said fractured bone 412, said first cylindrical sleeve 422 and said second cylindrical sleeve 423 take a cask configuration projecting outside the narrow sections 426 and 427 respectively, with a subsequent shortening of the longitudinal dimension of the two sleeves 422 and 423; in the preferred embodiment with the fillets 424a and 425a, in the final shape, the fillets 424a and 425a take a cask stave configuration, with a subsequent shortening of the longitudinal dimension of the two sleeves 422 and 423.

The tongue-shaped appendixes 430 and 431, when passing from the initial shape to the final shape, slide in the tongue housings 432 and 433, and also in said final shape the tongue-shape appendixes 430 and 431 are inserted in the corresponding tongue housings 432 and 433.

Figure 31:
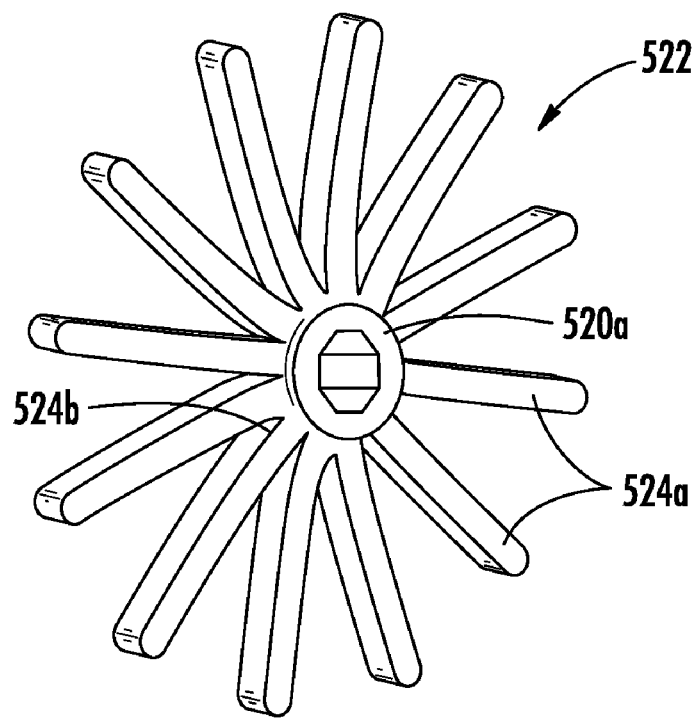
FIG. 31 schematically shows a perspective view of a further embodiment of an intramedullary nail according to the present invention.
Figure 32:
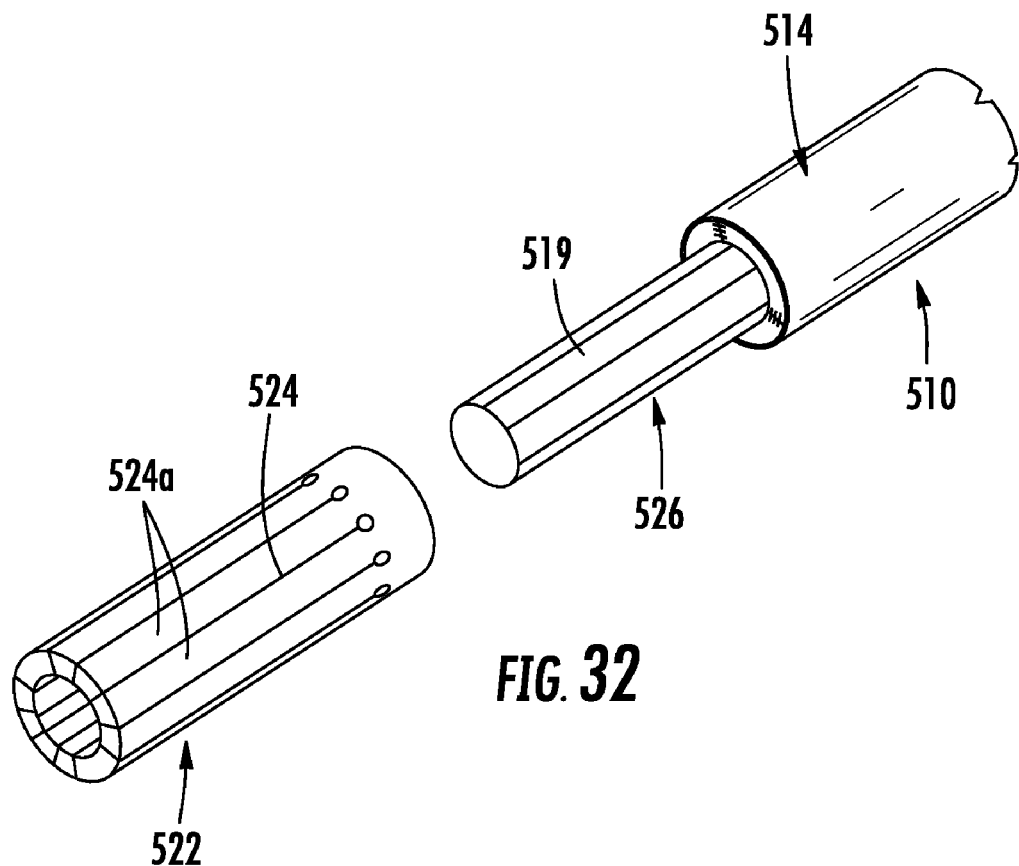
FIG. 32 schematically shows a perspective view of the nail of FIG. 31, during the assembling step.

Referring now to FIGS. 31 and 32 a sixth embodiment of intramedullary nail, according to the present invention, is shown and globally indicated with 510, suitable for insertion in a fractured elongate bone 12.

The nail 510 comprises a substantially straight stem 514 extending between a proximal end and a distal end and having at the two ends shape-memory elements 520 for fixing the nail 510 to the fractured bone.

An element 520a realised with a shape-memory material consists of a cylindrical sleeve 522 comprising a plurality of longitudinal cuts 524 crossing the thickness of the cylindrical sleeve 522, said cuts 524 starting from an end of the sleeve 522 and abutting in corresponding grooves 524b. The grooves 524b of the cuts 524 are shaped according to a circumference arc.

The stem 514 has, in correspondence with each end, a narrow section 526 defining a seat 519, wherein the cylindrical shape-memory sleeve 522 is worn, so that the free end of the foils 524a is turned outside the stem 514. More precisely, in the example of FIGS. 31 and 32, the narrow section 526 has an outer prismatic shape, for example in the shape of a regular octagonal prism, corresponding to an inner conjugated prismatic shape, for example in the shape of a regular octagonal prism, of the central hole of the cylindrical sleeve 522.

It is specified that the cylindrical sleeve 522, so worn in the narrow section 526, is fixed therein, using for the fixation an area of the cylindrical sleeve 522 being opposite to the starting end of said cuts 524.

The above description corresponds to the first shape, or first shape, wherein the shape-memory elements 520 are retractably housed in the narrow section 526. In the final shape, or second shape, the free ends of the foils 524 bend outside the stem 524, the foils 524a thus positioning in a substantially radial way projecting from the narrow section 526.

Figure 33:
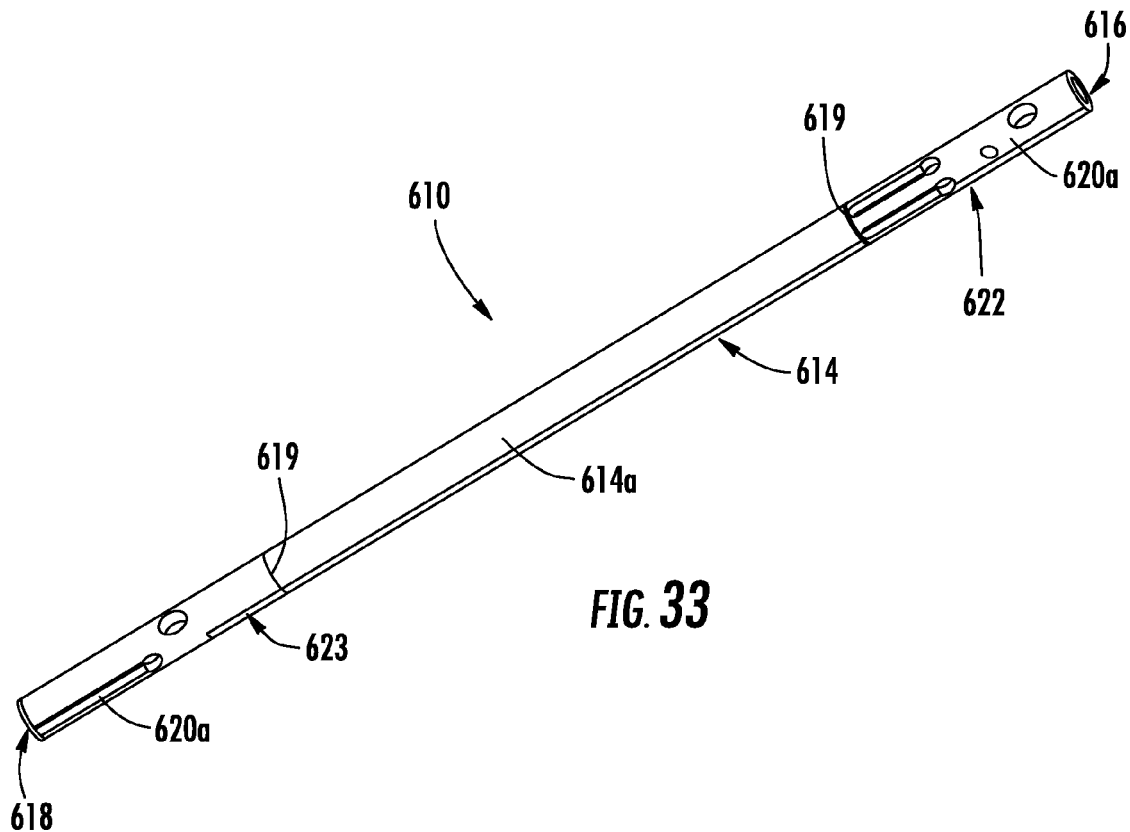
FIG. 33 schematically shows a perspective view of a further embodiment of an intramedullary nail according to the present invention.
Figure 34:
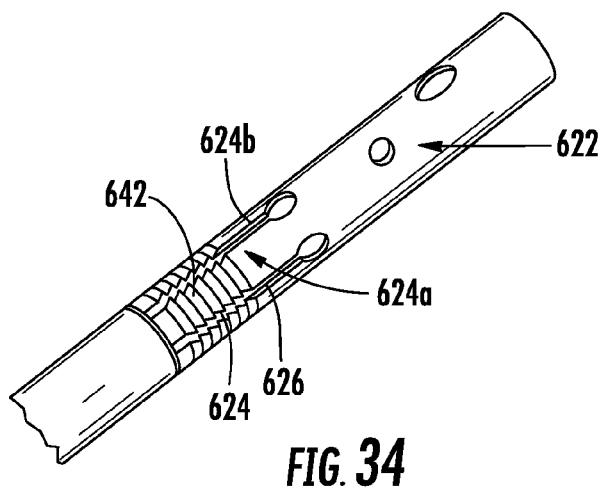
FIG. 34 schematically shows an enlarged perspective view of a portion of the nail of FIG. 33.

Referring now to FIGS. 33-34, a seventh embodiment of intramedullary nail, according to the present invention, is shown and globally indicated with 610, suitable for insertion in a fractured elongate bone 12.

The nail 610 comprises a substantially straight stem 614 extending between a proximal end 616 and a distal end 618.

The stem 614 comprises in correspondence with at least one of the two ends 616 and 618 shape-memory elements 620.

An element 620a realised with a shape-memory material for example at the proximal end 616, consist of a first cylindrical sleeve 622 comprising a plurality of longitudinal cuts 624 crossing the thickness of the cylindrical sleeve 622, said cuts 624 starting from an end of the sleeve 622 and abutting in corresponding grooves 624b.

The cuts 624 are preferably equally spaced around the cylindrical sleeve 622 and they define a plurality of foils 624a. In the example of the figures, the foils 624 are four; the grooves 624b of the cuts 624 are shaped according to a circumference arc. Ring-shaped grooves 642 are also provided, realised in correspondence with the free ends of the foils 624a: said ring-shaped grooves 642 are broken, along the circumference, by the cut 624 crossing.

The stem 614 has, in correspondence with the proximal end 616, a first narrow section 626, which defines a seat 619, wherein the cylindrical sleeve 622 is retractably worn, so that the free end of the foils 624a is turned towards a stem central portion 614a and it abuts in correspondence with the stem outer diameter change, wherein the first narrow section 626 is provided. Preferably, the first narrow section 626 has an outer prismatic shape corresponding to an inner conjugated prismatic shape of the central hole of the first cylindrical sleeve 622.

The foils 624a are realised with a shape-memory material and the first cylindrical sleeve 622, retractably worn in the first narrow section 626, is fixed therein, using for the fixation an area of the cylindrical sleeve 622 being opposite to the starting end of said cuts 624.

The above description corresponds to the initial shape, or first shape, wherein the foils 624a are retractably housed in the narrow section 626, i.e. they do not projects with respect to the stem 614. In the final shape, or second shape, the free ends of the foils 624a bend outside the stem, the foils 624a thus positioning in a substantially radial way projecting with respect to the narrow section 626.

An application method, according to the present invention, of said intramedullary nail in said elongate bone comprises: a location step of said nail in said elongate bone, to mend the fracture;
an activation step of said plurality of elements realised with at least a shape-memory material, taking said final form corresponding to a fixation of the nail to said fractured bone.

The operation of the intramedullary nail, suitable for insertion in a fractured elongate bone is hereafter described with reference to FIGS. 1-15.

In the case of the first embodiment of the intramedullary nail 10, the nail 10 is positioned in said elongate bone 12, in the initial shape thereof, with the free ends 21 of the elements 20 substantially not projecting from the side surface of the stem 14.

Afterwards, in order to fix the nail 10 to said bone 12, said shape-memory elements 20 are activated, so that the free ends 21 tend to be projects outwards the stem 14, with a subsequent interference of these free ends 21 with respect to the bone portion surrounding said stem 14: this interference causes in practise a grip, solidly fixing said nail 10 in the bone 12.

It must be noticed that the inserts 23 are fixed alternatively with respect to each other not to create a torsion or rotation effect when stabilising the nail 10 on the bone 12.

It is also worth underlining that the stem 14 is preferably a cylindrical tubular body: the central hole serves to have an improved thermal exchange, helping thus in activating the elements 20.

The main advantage reached by the intramedullary nail suitable for insertion in a fractured elongate bone, as well as by the application method of said nail into said bone, according to the present invention, stays in that it extremely simplifies the fixing step of the intramedullary nail inserted in the bone: the expansion of the shape-memory elements in fact occurs without a manual intervention of the mechanical type, since the shape-memory material used in the nail of the invention expands instead by means of heat absorption.

A nail offering a minimum invasiveness is thud obtained for being inserted.

A further advantage of the intramedullary nail according to the present invention is that of being of simple production, thanks to the reduced number of different pieces. It is to be noted in fact that, as above described, the inserts are similar.

Another advantage of the present invention stays in that the nail comprises a plurality of shape-memory inserts, which can be easily inserted in the stem.

In this regard, the stem realised with the two half-cylinders is particularly advantageous for allowing the insertion of the inserts 23.

Another advantage of the shape-memory inserts stays in that they are structurally independent from the nail stem. This allows to realise a stem of a non shape-memory material with substantial reduction of the production cost.

Moreover, the insertion by pressure of the inserts in the slots, has the advantage of realising an easy connection of the inserts with the nail stem, avoiding possible welds.

Another advantage of the present invention stays in that the taking of the first and of the second shape by the elements 20 is facilitated by the use of the sheathing jacket.

The jacket in fact allows maintaining the memory elements in the retractable position during the insertion in the medullary channel, for avoiding the risk that the body heat determines a shape variation before the nail is completely arranged in the bone.

Another advantage of the sheathing jacket with respect to the stem is obtained by means of an external tool.

A further advantage of the tubular jacket also stays in that it facilitates the extraction of the nail from the bone.

In this regard, it is highlighted that, during a possible extraction of the nail according to the invention, it is worth inserting, in the hole of the tubular body of the stem, an insert which reduces the temperature of the nail so as to cause a phase change in the material structure, thus obtaining a lower bending resistance by the shape-memory elements.

Obviously, a technician of the field, can bring several modifications to the above described intramedullary nail to be inserted in a fractured elongate bone and to the application method of said nail in said bone, so as to meet specific and contingent needs, all the modifications being however within the scope of protection of the present invention as defined by the following claims.

The invention claimed is:

1. An intramedullary nail suitable for insertion in a fractured elongate bone, comprising:
   a stem extending between a proximal end and a distal end,
   a plurality of shape-memory elements which at least include a shape-memory material, and
   a plurality of seats formed in the stem for housing said shape-memory elements,
   wherein said shape-memory elements are suitable to assume a first rest configuration in which said shape-memory elements are arranged inside the respective seats and a second use configuration in which said shape-memory elements project from the respective seats,
   wherein the nail includes inserts, structurally independent from the stem and comprising at least one of said shape-memory elements, each of said inserts being suitable to be arranged in a corresponding seat, and
   wherein each insert has substantially a fork-like shape and is made of a plurality of metallic foils stacked onto each other and consisting of shape-memory material, the metallic foils being held together by a pair of blocking pins inserted transversally to the metallic foils for ensuring a stable assembly of the metallic foils.

2. An intramedullary nail suitable for insertion in a fractured elongate bone, comprising:
   a stem extending between a proximal end and a distal end,
   a plurality of shape-memory elements which are made of at least a shape-memory material, and
   a plurality of seats formed in the stem for housing said shape-memory elements, said shape-memory elements are suitable to assume a first configuration of rest in which said shape-memory elements are arranged inside the respective seats and a second configuration of use in which said shape-memory elements project from the respective seats,
   wherein said shape-memory elements are structurally independent from the stem,
   wherein the nail comprises a tubular jacket for sheathing the stem, the tubular jacket having the function of retaining the shape-memory elements in the first configuration of rest, the jacket comprising a side wall and a plurality of transversal elongate holes made on the side wall, wherein the jacket and the stem can be shifted with respect to each other along a longitudinal axis of the stem from a first operative position in which the side wall of the jacket retains the shape-memory elements in the first configuration of rest, and a second operative position in which the transversal holes of the jacket are aligned with the seats of the stem, so as to allow the arrangement of the shape-memory elements projecting from the respective seats, and
   wherein a control screw, suitable to be rigidly connected to a head portion of the stem, causes an axial shift of the stem with respect to the jacket, when the control screw is rotated around its own axis.

3. The intramedullary nail according to claim 2, wherein the nail comprises an internally hollow tube suitable to be rigidly connected to a head portion of the jacket and in which the control screw is housed within the hollow tube with clearance.

4. The intramedullary nail according to claim 3, wherein the internally hollow tube is inserted in a bearing sleeve, said bearing sleeve being configured to maintain the jacket axially firm during the shift of the stem.

5. The intramedullary nail according to claim 4, wherein a cylindrical body is welded on the head portion of the jacket, said cylindrical body having an internal threading onto which a corresponding threading of the internally hollow tube is screwed, and wherein the cylindrical body is provided with a pair of recesses configured to receive corresponding teeth of the bearing sleeve.

6. The intramedullary nail according to claim 2, wherein the head portion of the stem is provided with a threaded portion suitable to engage a corresponding threaded portion of the control screw.

* * * * *